United States Patent [19]
Griffin et al.

[11] Patent Number: 5,279,956
[45] Date of Patent: Jan. 18, 1994

[54] ACTIVATED PROTEIN C POLYPEPTIDES AND ANTI-PEPTIDE ANTIBODIES, DIAGNOSTIC METHODS AND SYSTEMS FOR INHIBITING ACTIVATED PROTEIN C

[75] Inventors: John H. Griffin, Del Mar; Rolf M. Mesters, La Jolla, both of Calif.

[73] Assignee: The Scripps Research Institute, La Jolla, Calif.

[21] Appl. No.: 720,189

[22] Filed: Jun. 24, 1991

[51] Int. Cl.$^5$ .................. A61K 37/02; A61K 39/00; C12N 9/00; C07K 15/00
[52] U.S. Cl. .................................. 435/183; 435/692; 435/90.21; 435/240.27; 436/536; 424/85.8; 514/12; 530/328; 530/326; 530/384; 530/380; 530/381; 530/382; 530/383; 530/389.3; 530/388.26; 530/388.25; 530/324; 530/412
[58] Field of Search .................. 424/85.8; 435/69.2, 435/70.21, 240.27, 536, 183; 514/12; 530/328, 326, 324, 387, 380, 381, 382, 383, 384, 389.3, 308.26, 388.25, 412; 436/536

[56] References Cited

U.S. PATENT DOCUMENTS

| | | |
|---|---|---|
| 32,011 | 10/1885 | Zimmerman et al. |
| 4,361,509 | 11/1982 | Zimmerman et al. ............... 424/85 |
| 4,834,976 | 5/1989 | Rosok et al. |
| 4,918,163 | 4/1990 | Young et al. |
| 5,057,598 | 10/1991 | Pollack et al. |

FOREIGN PATENT DOCUMENTS 160457 11/1985 European Pat. Off.

OTHER PUBLICATIONS

Waldmann Science 252:1657–1662 1991.
Dahlback, et al., J. Clin. Invest., 66: 583–591 (1980).
Heeb, et al., *Thrombosis Res.*, 52: 33–43 (1988).
Ohlin, et al., Biochem., 29: 644–651 (1990).
Plutzky, et al., *Proc. Natl. Acad. Sci. USA*, 83: 546–550 (1986).
Solymoss, et al., J. Biol. Chem., 263: 14884–14890 (1988).
Suzuki, et al., *J. Biol. Chem.*, 257: 6556–6564 (1982).
Vehar, et al., Biochem., 19: 401–410 (1980).
Foster, et al Proc Natl Acad Sci 82:4673–4677 1985.

*Primary Examiner*—Christina Chan
*Assistant Examiner*—Donald Adams
*Attorney, Agent, or Firm*—Douglas A. Bingham; Thomas Fitting; April C. Logan

[57] ABSTRACT

The present invention describes APC polypeptides and anti-peptide antibodies capable of inhibiting activated Protein C anticoagulant activity. The polypeptide and antibody are useful in diagnostic methods and systems for measuring APC in vascular fluid samples. In addition, the polypeptide and anti-peptide antibody are useful in therapeutic methods for inhibiting APC in a human patient.

28 Claims, 7 Drawing Sheets

ACTIVATED PROTEIN C POLYPEPTIDES AND ANTI-PEPTIDE ANTIBODIES, DIAGNOSTIC METHODS AND SYSTEMS FOR INHIBITING ACTIVATED PROTEIN C this invention was made with the support of the U.S. Government, and the U.S. Government has certain rights in the invention pursuant to National Institutes of Heal Contract HC-31950.

TECHNICAL FIELD

The present invention relates to polypeptides and anti-peptide antibodies useful for therapeutic methods and compositions for inhibiting activated protein C (APC). In addition, the polypeptides and antibodies are useful for inhibiting APC in diagnostic assays and in protein purification procedures where APC activity is not desirable.

BACKGROUND

Protein C (PC) is a member of the class of a vitamin K-dependent serine protease coagulation factors. Unlike the majority of coagulation factors, Protein C regulates blood coagulation by acting an a natural anticoagulant that circulates in the blood in an inactive form that requires proteolytic activation to generate the anticoagulant enzyme. The activated form of Protein C, APC, inhibits blood coagulation at the levels of Factor V and VIII in the clotting cascade.

Similar to most other zymogens of extracellular proteases, Protein C has the core structure of the chymotrypsin family having insertions and N-terminus extensions that enable regulation of the zymogen and the enzyme. See Owen W., in "Hemostasis and Thrombosis: Basic Principles and Clinical Practice", Colman et al., eds, pp. 235-241, J. B. Lippincott Co. (Philadelphia), 1987. The isolated zymogen from human consists of two polypeptide chains, a heavy and a light chain having the respective molecular weights of 41,000 and 21,000 daltons, linked by a single disulfide. The light chain is 155 amino acid residues in length, the first 11 glutamate residues of which reside within the first 35 amino acid residues and are gamma-carboxylated. The zymogen heavy chain is 262 amino acid residues long which is cleaved to a final 250 amino acid residues in length upon activation.

Protein C is composed of domains with discrete structure and function. See Foster et al., *Proc. Natl. Acad. Sci. USA*, 82:4673-4677 (1985) and Plutzky et al., *Proc. Natl. Acad. Sci. USA*, 83:546-550 (1986). The light chain contains an animo-terminal gamma-carboxyglutamic acid (Gla) region which is followed by two domains that are homologous to domains in the epidermal growth factor (EGF) precursor. The serine protease activity resides in the heavy chain. Ohlin et al., *Biochem.*, 29:644-651 (1990).

The zymogen is activated by the action of thrombin at the site between the arginine residue at position number 12 and the leucine residue at position 13. See Kisiel, *J. Clin. Invest.*, 64:761-769, (1976); Marlar et al., *Blood*, 59:1067-1072 (1982). Other proteins including Factor Xa (Haley et al., *J. Biol. Chem.*, 264:16303-16310 (1989), Russell's viper venom and trypsin (Esmon et al., *J. Biol. Chem.*, 251:2770-2776 (1976) have also been shown of enzymatically cleave inactive protein C to its activated form. Activated protein C hydrolyzes arginine esters and related substrates via a core triad of catalytic amino acid residues which occur at Ser-201, His-56, and Asp-102 of the heavy chain. The triad forms a hydrophobic substrate binding pocket. The enzyme's specificity is restricted to a small number of protein substrates; blood coagulation cofactors, activated Factors V and VIII, are the only known macromolecular substrates for the proteolytic inactivation by activated protein C. See Kisiel et al., *Biochem.*, 16:5824-5831 (1977); Vehar et al., *Biochem.*, 19:401-410 (1980); and Walker et al., *Biochim. Biophys. Acta.*, 571:333-342 (1979).

Thrombin, the major physiological protein C activator, activates protein C slowly in purified systems, plasma, or blood, when in the presence of physiolgical concentrations of calcium. A membrane-bound thrombin receptor called thrombomodulin has been identified which accelerates protein C activation. Esmon et al., *Proc. Natl. Acad. Sci. USA*, 78:2249-2252 (1981). Liberated thrombin binds to thrombomodulin on the luminal surface of endothelial cells and undergoes an increase in specificity for circulating protein C. Calcium is required for this process and is bound to calcium-binding domains in the EGF-like regions of protein C. Additional studies have revealed that the membrane-lipid domain of protein C, the vitamin-K dependent Gla domain, is also required for activation of protein C. Esmon et al., in "Progress in Vascular Biology, Hemostasis, and Thrombosis", Ruggeri et al., eds., Annals of The New York Academy of Sciences, Vol. 614:30-43 (1991).

Inhibitors of activated protein C which function to inhibit anticoagulant activity have been characterized. Malar and Griffin characterized a partially purified inhibitor in plasma, the binding of which to activated protein C results in the complete loss of anticoagulant and esterolytic activities. Marlar et al., *J. Clin. Invest.*, 66:1186-1193 (1980). Suzuki and collaborators have purified the heparin-dependent inhibitor and determined that the inhibition of the activated enzyme occurred through the formation of an enzyme-inhibitor complex accompanied with the proteolytic modification of the inhibitor by the enzyme. Suzuki et al., *J. Biochem.*, 95:187-195 (1984). More recently, a heparin-independent inhibitor of activated protein C has been characterized. Heeb et al., *J. Biol. Chem.*, 265:2365-2369 (1990). The active site of this enzyme called $\alpha_1$-antitrypsin occurs at the methionine residue at position 358 the binding of which results in the inactivation of activated protein C. Patients with a combined deficiency of Factor V and Factor VIII have been shown to also lack the heparin-dependent form of inhibitor. Marlar et al., supra, (1980).

Clinical evidence for a regulatory role of protein C as well as its inhibitors is abundant. A family having a protein C deficiency was identified in 1981 having the symptoms of episodes of severe recurrent venous thrombosis. Patients having abnormal protein C which cannot be activated by the thrombin-thrombomodulin complex have also been identified. Comp et al., *Blood*, 63:15-21 (1984); Griffin et al., *Blood*, 62:301a (1983); and Sala et al., *Blood*, 63:671-675 (1984).

Neonatal purpura fulminans is a condition in newborn infants who are homozygous for deficiency of protein C and consequently, develop severe clotting in the capillaries of the skin. Branson et al., *Lancet*, 2:1165-1168 (1983); Seligsohn et al., *N. Eng. J. Med.*, 310:559-562 (1984). In view of the properties of activated protein C, a deficiency of the enzyme might result in a hypercoaguable state.

One advantage of this condition is that coagulation cofactors V and VIII, which are normally inactivated by activated protein C, remain in an activated state. Methods for purifying Factor V and Factor VIII are well known in the art. See, for example, U.S. Pat. Re. No. 32,001; EPO Publication No. 160,457; Vehar et al., supra; Dahlback et al., *J. Clin. Invest.*, 66:583-591 (1980); and Suzuki et al., *J. Biol. Chem.*, 257:6556-6564 (1982). Methods for purifying the activated forms of Factor V and Factor VIII are not available as the activated factors are rapidly degraded in the blood under normal conditions by activated protein C.

In the present invention, synthetic polypeptides corresponding to the heavy chain domain of protein C have been discovered which have the ability to inhibit the anticoagulant properties of activated protein C. The present invention, thus, contemplates a method for purifying Factor Va and Factor VIIIa through the use of an activated protein C-inhibiting amount of a composition comprising a protein C derived synthetic polypeptide, antibody, or a monoclonal antibody. The method is based on the discovery described herein of inhibitors of activated protein C and their demonstrated utility in inhibiting the enzyme in vitro.

No polypeptides having this activity have ever been described before this present invention. In fact, protein C from bovine has only been proteolytically cleaved into two fragments. The larger one consists of the entire light chain of protein C having two epidermal growth factor-like domains and the Gla domain along with 23 heavy chain residues. Ohlin et al., supra. This fragment exhibits inhibitory activity towards activated protein C but it lacks the regions defined in the present invention which specify the smallest peptide which inhibits activated protein C.

BRIEF SUMMARY OF THE INVENTION

Polypeptide-defined regions of APC have now been discovered that define polypeptides useful for inhibiting APC- mediated anticoagulation.

Thus, the present invention contemplates a variety of APC polypeptides comprising no more than about 100 amino acid residues that have the capacity to inhibit APC activity and include an amino acid residue sequence that corresponds to a portion of the heavy chain of PC.

In a related embodiment, the present invention contemplates an antibody comprising antibody molecules that inhibits APC and that immunoreacts with APC and a PC polypeptide of this invention having an amino acid residue sequence represented by the formula: PATLSQTIVPICLPDSGLAERE (SEQ ID NO 1 from residue 266 to residue 287).

A method for inhibiting APC in a patient is also contemplated that comprises administering to said patient an APC-inhibiting amount of an APC inhibitor of this invention, namely a protein C polypeptide or an anti-PC antibody of this invention.

Further contemplated is an improvement to methods for purifying blood coagulation Factor VIII or Factor V protein from plasma concentrate, the improvement comprising the step of contacting said plasma or concentrate with an APC-inhibiting amount of a protein C polypeptide or an antibody of this invention.

In addition, the invention contemplates an in vitro method for inhibiting APC in an aqueous composition with an APC-inhibiting amount of a protein C polypeptide or anti-PC antibody of this invention.

BRIEF DESCRIPTION OF THE DRAWINGS

In the drawings, forming a portion of this disclosure.

DETAILED DESCRIPTION OF THE INVENTION

A. Definitions

Figure 1:
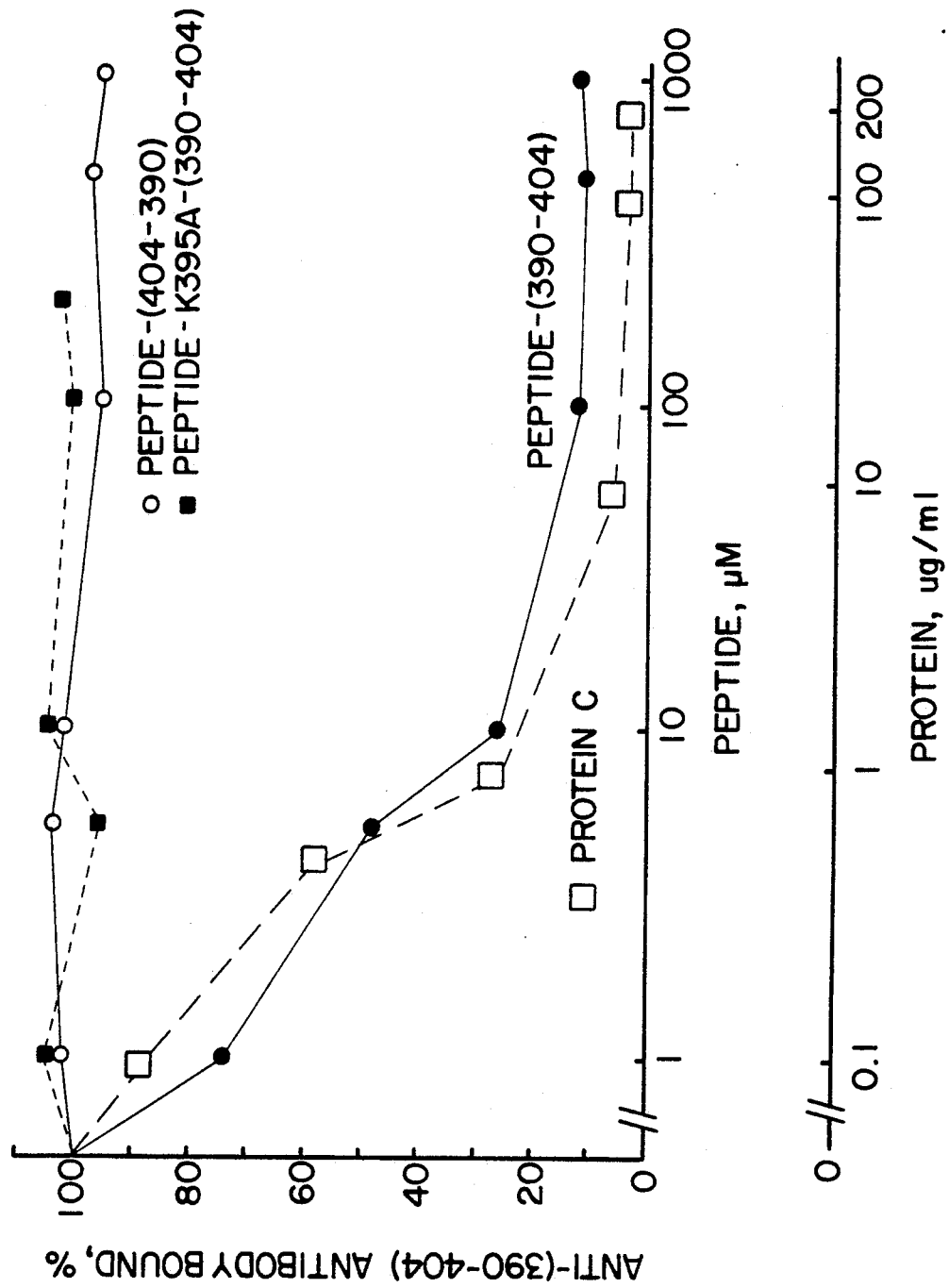
FIG. 1 illustrates anti-(390-404) antibody binding to immobilized Protein C (PC) in the presence of fluid-phase PC, peptide-(390-404), -(404-390) and -K395A-(390-404). Ten micrograms/milliliter ($\mu$g/ml) PC were coated on microtiter wells and non-specific binding sites were subsequently blocked with 10% bovine serum albumin (BSA). Before admixing 2 $\mu$g/ml anti-(390-404) antibody to PC-coated wells, the anti-(390-404) antibody was admixed with 0 to 200 $\mu$g/ml of either PC, 0 to 1000 $\mu$M peptide (-390-404), 0 to 1000 $\mu$M peptide-(404-390), or 0-200 $\mu$M peptide-K395A-(390-404) for 30 minutes at 37° C. Following biotinylated-goat-anti-rabbit-IgG and streptavidin-alkaline-phosphatase immunoreactions as described in Example 2c, bound anti-(390-404) antibody was detected by addition of 5 milligrams/milliliter (mg/ml) p-nitrophenylphosphate in 0.1M diethanolamine at pH 9.6 followed by measuring of the change in absorbance at 405 nm over time. The amount of anti-(390-404) specifically bound to PC coated wells in the absence of any competing protein was defined as 100%. Dashed lines with open squares indicate the bound anti-(390-404) antibody to PC in the presence of 0 to 200 $\mu$g/ml PC, solid lines with solid circles indicate anti-(390-404) antibody bound to immobilized PC in the presence of 0 to 1000 $\mu$M peptide-(390-404), solid lines with open circles indicate anti-(390-404) antibody bound to immobilized PC in the presence of 0 to 1000 $\mu$M peptide-(404-390), and dashed lines with solid squares indicate anti-(390-404) bound to immobilized PC in the presence of 0 to 200 $\mu$M peptide-K395A-(390-404). Results are discussed in Example 2c.

Amino Acid Residue: The amino acid residues described herein are preferred to be in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, J. Biol. Chem., 3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulas whose left and right orientation is in the conventional direction of amino-terminus to carboxy-terminus. Furthermore, it should be noted that a dash at the beginning or end of an amino acid residue sequence indicates either a peptide bond to a further sequence of one or more amino acid residues or a covalent bond to a carboxyl or hydroxyl end group. The absence of a dash indicates a polypeptide with no additional amino acid residues other than those specified.

Activated Protein C: Activated Protein C refers to Protein C that is cleaved proteolytically by thrombin to yield an activated protein C (APC) which inactivates coagulation Factors Va and VIIIa thus inhibiting coagulation.

Activated Protein C Inhibitor: A PC polypeptide or anti-PC antibody or monoclonal antibody of this invention that inhibits APC in an APC activity assay.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between and antigenic determinant-containing molecule and a molecule containing an antibody combining site such as a whole antibody molecule or a portion thereof.

Factor V: Factor V is a high molecular weight protein that, when activated by thrombin, can accelerate the conversion of prothrombin to thrombin by Factor Xa which promotes coagulation. Activated factor Va is inactivated by activated Protein C to inhibit the coagulation process.

Factor VIII: Factor VIII, also called the antihemophilic factor in blood coagulation, is a high molecular weight protein involved in the activation of Factor X in concert with Factor IXa. Activated Factor VIIIa is inactivated by activated Protein C to inhibit the coagulation process.

Factor X: Factor X is a zymogen of a serine protease which has a molecular weight of 55,000. When activated, Factor Xa in concert with Factor Va, causes the conversion of prothrombin to thrombin which promotes coagulation.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

Polypeptide and Peptide: Polypeptide and peptide are terms used interchangeably herein to designate a linear series of amino acid residues connected one to the other by peptide bonds between the alpha-amino and carboxy groups of adjacent residues.

Protein: Protein C (PC) is a vitamin K-dependent serine protease zymogen and is homologous with other known vitamin K-dependent serine proteases. In the presence of endothelial cell thrombomodulin and thrombin, Protein C is activated to a serine protease, APC, and becomes a potent inhibitor of blood coagulation by inactivating Factor Va and Factor VIIIa.

Protein S: Protein S (PS) is a vitamin K-dependent plasma protein which serves as a co-factor to activated Protein C in the inactivation of Factors Va and VIIIa.

Serine Proteases: Serine proteases are a family of protein-cleaving (proteolytic) enzymes of which activated Protein C is a member.

Synthetic Peptide: Synthetic Peptide refers to a chemically produced chain of amino acid residues linked together by peptide bonds that is free of naturally occurring proteins and fragments thereof.

B. Polypeptides

As used herein, the phrase "PC polypeptide" refers to a polypeptide having an amino acid residue sequence that includes a sequence that corresponds, and preferably is identical, to a portion of the heavy chain of protein C molecule. The protein C molecule consists of a 155 amino acid residue light chain and a 262 amino acid residue heavy chain. The amino acid residue sequence of protein C heavy chain is listed as SEQ ID NO 1 in the sequence listing. The amino acid residue positions of PC-derived polypeptides disclosed in the specification are designated by their position relative to the PC heavy chain and not to the residue numbers as shown under every fifth amino acid residue in the Sequence Listing. For example, the PC heavy chain listed in SEQ ID NO 1 begins at amino acid residue position 158 and ends at 419 which corresponds to amino acid residue positions 1 through 262 as shwon in the listing.

In one embodiment, a PC polypeptide of the present invention comprises no more than about 100 amino acid residues, preferably no more than about 60 residues, more preferably no more than about 30 residues, and includes an amino acid residue sequence represented by the formula: —YGVYTXVSRYLDWIH— (SEQ ID NO 2 from residue 390 to residue 404), wherein X is either lysine (K) or alanine (A). This polypeptide defines a conserved native epitope on PC and has the capacity to inhibit activated protein C according to the teachings herein. In preferred embodiments, the polypeptide has an amino acid residue sequence represented by a formula selected from the group consisting of: YGVYTKVSRYLDWIH (SEQ ID NO 1 from residue 390 to residue 404), YGVYTKVSRYLDWIHGHIRDK (SEQ ID NO 1 from residue 390 to residue 410), CGLLHNYGVYTKVSRYLDWIH (SEQ ID NO 1 from residue 384 to residue 404), CGLLHNYGVYTKVSRYLDWIHGHIRDK (SEQ ID NO 1 from residue 384 to residue 410), SGLLHNYGVYTKVSRYLDWIHGHIRDK (SEQ ID NO 3 from residue 384 to residue 410), SGLLHNYGVYTKVSRYLDWIH (SEQ ID NO 3 from residue 384 to residue 404), and YGVYTAVSRYLDWIH (SEQ ID NO 4 from residue 390 to residue 404).

In a related embodiment, a PC polypeptide of the present invention comprises no more than about 100 amino acid residues, preferably no more than about 60 residues, more preferably no more than about 30 residues, and includes an amino acid residue sequence represented by the formula: —YGVYTKVSR— (shown in SEQ ID NO 1 from residue 390 to residue 398). This polypeptide defines a conserved native epitope on PC and has the capacity to inhibit activated protein C according to the teachings herein. In preferred embodiments, the polypeptide has an amino acid residue sequence represented by a formula selected from the group consisting of: YGVYTKVSR (SEQ ID NO 1 from residue 390 to residue 398), CGLLHNYGVYTKVSR (SEQ ID NO 1 from residue 384 to residue 398), and SGLLHNYGVYTKVSR (SEQ ID NO 3 from residue 384 to residue 398).

Another related embodiment of the present invention contemplates a PC polypeptide that comprises no more than about 100 amino acid residues, preferably no more than about 60 residues, more preferably no more than about 30 residues, and includes an amino acid residue sequence represented by the formula: —VSRYLDWIH—, (shown in SEQ ID NO 1 from residue 396 to residue 404). This polypeptide defines a conserved native epitope on PC and has the capacity to inhibit activated protein C according to the teachings herein. In preferred embodiments, the polypeptide has an amino acid residue sequence represented by a formula selected from the group consisting of: VSRYLDWIH (SEQ ID NO 1 from residue 396 to residue 404), and VSRYLD- WIHGHIRDK (SEQ ID NO 1 from residue 396 to residue 410).

A further related embodiment of the present invention contemplates a PC polypeptide that comprises no more than about 100 amino acid residues, preferably no more than about 60 residues, more preferably no more than about 30 residues, and includes an amino acid residue sequence represented by the formula: —TRRGDSPWQVVLLDS—, (shown in SEQ ID NO 1 from residue 176 to residue 190). This polypeptide defines a conserved native epitope on PC and has the capacity to inhibit activated protein C according to the teachings herein. In preferred embodiments, the polypeptide has an amino acid residue sequence represented by the formula: TRRGDSPWQVVLLDS (SEQ ID NO 1 from residue 176 to residue 190).

Another related embodiment of the present invention contemplates a PC polypeptide that comprises no more than about 100 amino acid residues, preferably no more than about 60 residues, more preferably no more than about 30 residues, and includes an amino acid residue sequence represented by the formula: —DIKEVFVHPNYSKST—, (shown in SEQ ID NO 1 from residue 239 to residue 253). This polypeptide defines a conserved native epitope on PC and has the capacity to inhibit activated protein C according to the teachings herein. In preferred embodiments, the polypeptide has an amino acid residue sequence represented by the formula: DIKEVFVHPNYSKST (SEQ ID NO 1 from residue 239 to residue 253).

A further related embodiment of the present invention contemplates a PC polypeptide that comprises no more than about 100 amino acid residues, preferably no more than about 60 residues, more preferably no more than about 30 residues, and includes an amino acid residue sequence represented by the formula: —VLNFIKIPV—, (shown in SEQ ID NO 1 from residue 317 to residue 325). This polypeptide defines a conserved native epitope on PC and has the capacity to inhibit activated protein C according to the teachings herein. In preferred embodiments, the polypeptide has an amino acid residue sequence represented by the formula: VLNFIKIPV (SEQ ID NO 1 from residue 317 to residue 325).

Preferred PC polypeptides, their designations, and their protein C amino acid residue positions are shown in Table 1.

TABLE 1

| Polypeptide Designation | Amino Acid Residue Sequence |
|---|---|
| PC 390-404* | YGVYTKVSRYLDWIH |
| PC 390-410* | YGVYTKVSRYLDWIHGHIRDK |
| PC 384-404* | CGLLHNYGVYTKVSRYLDWIH |
| PC 384-410* | CGLLHNYGVYTKVSRYLDWIHGHIRDK |
| PC 384-410[1] | SGLLHNYGVYTKVSRYLDWIHGHIRDK |
| PC 384-404[2] | SGLLHNYGVYTKVSRYLDWIH |
| PC 390-404[3] | YGVYTAVSRYLDWIH |
| PC 390-398* | YGVYTKVSR |
| PC 384-398* | CGLLHNYGVYTKVSR |
| PC 384-398[4] | SGLLHNYGVYTKVSR |
| PC 376-404* | VSRYLDWIH |
| PC 396-410* | VSRYLDWIHGHIRDK |

*SEQ ID NO. 1.
[1]Ser substituted for Cys at residue position 384; SER ID NO 3.
[2]Ser substituted for Cys at residue position 384; SEQ ID NO 3.
[3]Ala substituted for Lys at residue position 395; SEQ ID NO 4.
[4]Ser substituted for Cys at residue position 384; SEQ ID NO 3.

Preferably, a PC polypeptide of this invention is further characterized by its ability to immunologically mimic an epitope (antigenic determinant) expressed by PC.

As used herein, the phrase "immunologically mimic" in its various grammatical forms refers to the ability of a PC polypeptide of this invention to immunoreact with an antibody of the present invention that immunoreacts with a native epitope of PC as defined herein.

It should be understood that a subject polypeptide need not be identical to the amino acid residue sequence of PC, so long as it includes the required sequence and is able to inhibit activated protein C (APC) in an assay for APC activity such as is described herein.

A subject polypeptide includes any analog, fragment or chemical derivative of a polypeptide whose amino acid residue sequence is shown herein so long as the polypeptide is capable of inhibiting APC. Therefore, a present polypeptide can be subject to various changes, substitutions, insertions, and deletions where such changes provide for certain advantages in its use. In this regard, a PC polypeptide of this invention corresponds to, rather than is identical to, the sequence of protein C where one or more changes are made and it retains the ability to inhibit APC in one or more of the assays as defined herein for determining APC activity.

The term "analog" includes any polypeptide having an amino acid residue sequence substantially identical to a sequence specifically shown herein in which one or more residues have been conservatively substituted with a functionally similar residue and which displays the ability to inhibit APC as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

A polypeptide is free of homoserine lactone when there is no detectable homoserine lactone present in the polypeptide when subjected to conventional amino acid analysis able to indicate the presence of homoserine lactone or other amino acids. Amino acid analysis methods suitable to detect homoserine lactone are generally well known in the art.

The term "fragment" refers to any subject polypeptide having an amino acid residue sequence shorter than that of a polypeptide whose amino acid residue sequence is shown herein.

When a polypeptide of the present invention has a sequence that is not identical to the sequence of protein C, it is typically because one or more conservative or non-conservative substitutions have been made, usually no more than about 30 number percent, and preferably no more than 10 number percent of the amino acid residues are substituted. Additional residues may also be added at either terminus of a PC polypeptide for the purpose of providing a "linker" by which the polypeptides of this invention can be conveniently affixed to a label or solid matrix, or carrier. Preferably, the linker residues do not form PC epitopes, i.e., are not similar in structure to PC.

Labels, solid matrices and carriers that can be used with the polypeptides of this invention are described hereinbelow.

Amino acid residue linkers are usually at least one residue and can be 40 or more residues, more often 1 to 10 residues, but do not form PC epitopes. Typical amino acid residues used for linking are tyrosine, cysteine, lysine, glutamic and aspartic acid, or the like. In addition, a subject polypeptide can differ, unless otherwise specified, from the natural sequence of PC by the sequence being modified by terminal-$NH_2$ acylation, e.g., acetylation, or thioglycolic acid amidation, by terminal-carboxyamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification.

When coupled to a carrier to form what is known in the art as a carrier-hapten conjugate, a PC polypeptide of the present invention is capable of inducing antibodies that immunoreact with PC. In view of the well established principle of immunologic cross-reactivity, the present invention therefore contemplates antigenically related variants of the polypeptides shown in Table 1 above and Table 2 in Examples. An "antigenically related variant" is a subject polypeptide that is capable of inducing antibody molecules that immunoreact with a polypeptide from Table 1 above and from Table 2 in Examples and PC.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A PC polypeptide of the present invention also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

A PC polypeptide can be used, inter alia, in the diagnostic methods and systems of the present invention as an APC inhibitor in methods to detect the presence in a body sample of a serum protein such as Factor V or Factor VIII whose level may be adversely affected by the presence of APC. A PC polypeptide can also be used to prepare an inoculum as described herein for the preparation of antibodies that immunoreact with epitopes on PC. In addition, a PC polypeptide can be used in vitro to inhibit the inactivation of Factor VIII or Factor V during procedures for purifying those factors as described herein. A PC polypeptide of this invention can also be used in the therapeutic methods of the present invention to inhibit activated protein C (APC).

C. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab'): portions of antibodies are prepared by the proteolytic reaction of papain and pepsin, respectively, on substantially intact antibodies by methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

An antibody of the present invention, i.e., an anti-PC antibody, comprises antibody molecules that inhibit activated protein C (APC) as described herein.

An anti-PC antibody is further characterized as being capable of immunoreacting with 1) isolated PC, preferably activated PC, and 2) a PC polypeptide of the present invention, and being substantially free of antibody molecules that immunoreact with the polypeptide: PATLSQTIVPICLPDSGLAERE (SEQ ID NO 1 from residue 266 to residue 287).

In preferred embodiments, an anti-PC antibody is characterized as being capable of immunoreacting with a polypeptide having an amino acid residue sequence represented by the formula selected from the group consisting of a polypeptide having an amino acid residue sequence represented by the formula selected from the group consisting of: YGVYTKVSRYLDWIH, TRRGDSPWQVVLLDS, DIKEVFVHPNYSKST, KRNRTFVLNFIKIPVVPHNEC, said sequences shown in SEQ ID NO 1 from residue 390 to residue 404, from residue 176 to residue 190, from residue 239 to residue 253, and from residue 311 to residue 331, respectively.

Particularly preferred anti-PC antibodies immunoreact with a PC polypeptide having a sequence that includes the epitope defined by the formula: —YG-VYTKVSR—, said sequence shown in SEQ ID NO 1 from residue 390 to residue 398. Most preferred are anti-PC antibodies that immunoreact with the polypeptide shown in SEQ ID NO 1 from residue 390 to residue 404.

Antibody immunoreactivity with PC-containing antigens can be measured by a variety of immunological assays known in the art. Exemplary immunoreaction of an anti-PC antibody with a PC-peptide is described in Example 2c3). Direct binding with PC isolated, APC, and with PC polypeptides can be assayed at least by the methods described in Examples 2c3) and 3.

By "substantially free" means that the antibody molecules do not immunoreact with the stated antigen at levels within one order of magnitude, and preferably within two orders of magnitude, of the levels of positive immunoreacting species of antigen.

An antibody of the present invention is typically produced by immunizing a mammal with an inoculum containing a PC polypeptide of this invention and thereby induce in the mammal antibody molecules having immunospecificity for PC polypeptide. The antibody molecules are then collected from the mammal and isolated to the extent desired by well known techniques such as, for example, by using DEAE Sephadex to obtain the IgG fraction. Exemplary antibody preparation methods are described herein at Example 2.

The preparation of antibodies against polypeptide is well known in the art. [See Staudt et al., *J. Exp. Med.*, 157:687–704 (1983)]. Briefly, to produce a peptide antibody composition of this invention, a laboratory mammal is inoculated with an immunologically effective amount of a PC polypeptide homolog, typically as present in a vaccine of the present invention. The anti-PC peptide antibody molecules thereby induced are then collected from the mammal and those immunospecific for both the PC polypeptide and APC are isolated to the extent desired by well known techniques such as, for example, by immunoaffinity chromatography.

To enhance the specificity of the antibody, the antibodies may be purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The word "inoculum" in its various grammatical forms is used herein to describe a composition containing a PC polypeptide of this invention as an active ingredient used for the preparation of antibodies against a PC polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier.

Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, dialdehydes such as glutaraldehyde, Klipstein, et al., *J. Infect. Dis.*, 147:318-326 (1983) and the like, or the use of carbodiimide technology as in the use of a water-soluble carbodiimide to form amide links to the carrier. For a review of protein conjugation or coupling through activated functional groups, see Aurameas, et al., *Scand. J. Immunol.*, 1:7-23 (1978). Alternatively, the heterobifunctional cross-linker SPDP (N-succinimidyl-3-(2-pyridyldithio) proprionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The techniques of polypeptide conjugation or coupling through activated functional groups presently known in the art are particularly applicable. See, for example, Aurameas, et al., *Scand. J. Immunol.* Vol. 8, Suppl. 7:7-23 (1978) and U.S. Pat. No. 4,493,795, U.S. Pat. No. 3,791,932 and U.S. Pat. No. 3,839,153. In addition, a site directed coupling reaction can be carried out so that any loss of activity due to polypeptide orientation after coupling can be minimized. See, for example, Rodwell et al., *Biotech.*, 3:889-894 (1985), and U.S. Pat. No. 4,671,958.

One or more additional amino acid residues may be added to the amino- or carboxy-termini of the polypeptide to assist in binding the polypeptide to form a conjugate. Cysteine residues, usually added at the carboxy-terminus of the polypeptide, have been found to be particularly useful for forming conjugates via disulfide bonds, but other methods well-known in the art for preparing conjugates may be used.

An anti-PC antibody can be used, inter alia, in the diagnostic methods and systems of the present invention as an APC inhibitor in methods to detect the presence in a body sample of a serum protein such as Factor V or Factor VIII whose level may be adversely affected by the presence of APC. An anti-PC antibody can also be used in vitro to inhibit the inactivation of Factor VIII or Factor V during procedures for purifying those factors as described herein. Anti-PC antibody of this invention can also be used in the therapeutic methods of the present invention to inhibit activated protein C (APC).

A preferred anti-PC antibody is a monoclonal antibody and is used herein as exemplary of an anti-PC antibody.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

A monoclonal antibody of this invention comprises antibody molecules that inhibit activated protein C (APC) as described herein. A monoclonal antibody of this invention is further characterized as being capable of immunoreacting with 1) isolated PC, preferably activated PC, and 2) a PC polypeptide of the present invention as described for the anti-PC antibodies of this invention.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature* 256:495-497 (1975), which description is incorporated by reference. The hybridoma supernates so prepared can be screened for the presence of antibody molecules that immunoreact with a PC polypeptide, or for inhibition of APC as described further herein.

Briefly, to form the hybridoma from which the monoclonal antibody composition is produced, a myeloma or other self-perpetuating cell line is fused with lymphocytes obtained from the spleen of a mammal hyperimmunized with a PC antigen, such as is present in a PC-containing lipoprotein particle, or with a PC polypeptide of this invention. The polypeptide-induced hybridoma technology is described by Niman et al., *Proc. Natl. Acad. Sci., U.S.A.*, 80:4949–4953 (1983), which description is incorporated herein by reference.

It is preferred that the myeloma cell line used to prepare a hybridoma be from the same species as the lymphocytes. Typically, a mouse of the strain 129 GlX+ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the radioimmunoassay (RIA) and the enzyme linked immunosorbent assay (ELISA) described in Examples 4 and 2, respectively.

A monoclonal antibody of the present invention can also be produced by initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

The monoclonal antibodies of this invention can be used in the same manner as disclosed herein for antibodies of the present invention.

For example, the monoclonal antibody can be used in the therapeutic, diagnostic or in vitro methods disclosed herein where inhibition of activated protein C is desired.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci. USA*, 86:5728–5732 (1989); and Huse et al., *Science*, 246:1275–1281 (1981).

Also contemplated by this invention is the hybridoma cell, and cultures containing a hybridoma cell that produce a monoclonal antibody of this invention.

D. Diagnostic Systems

The present invention also describes a diagnostic system, preferably in kit form, for assaying for the presence of Factor V or Factor VIII in a fluid sample where in activation of activated protein C (APC) is desirable according to the diagnostic methods described herein. A diagnostic system includes, in an amount sufficient to inhibit APC in at least one assay, a subject PC polypeptide and/or a subject antibody or monoclonal antibody, as a separately packaged reagent.

In another embodiment, a diagnostic system is contemplated for assaying for the presence of a PC polypeptide or anti-PC antibody in a body fluid sample such as for monitoring the fate of therapeutically administered PC polypeptide or anti-PC antibody. The system includes, in an amount sufficient for at least one assay, a subject PC polypeptide and/or a subject antibody as a separately packaged immunochemical reagent.

Instructions for use of the packaged reagent are also typically included.

As used herein, the term "package" refers to a solid matrix or material such as glass, plastic, paper, foil and the like capable of holding within fixed limits a polypeptide, polyclonal antibody or monoclonal antibody of the present invention. Thus, for example, a package can be a glass vial used to contain milligram quantities of a contemplated polypeptide or antibody or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence of or to quantitate a serum protein inhibited by APC and present in a sample, such as blood, plasma or serum, comprises a package containing at least one PC polypeptide of this invention. In another embodiment, a diagnostic system of the present invention for assaying for the presence or amount of a serum protein inhibited by and present in a sample can include an anti-PC antibody composition of this invention. Exemplary diagnostic systems utilizing an APC inhibitory polypeptide or antibody of this invention are described in Example 5.

In embodiments for detecting a subject PC polypeptide or an anti-PC antibody in a body fluid, a diagnostic system of the present invention can include a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$ indium of $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3-46 (1981). The techniques of protein conjugation or coupling through activated functional groups are particularly applicable. See, for example, Aurameas, et al., *Scand. J. Immunol.*, Vol. 8 Suppl. 7:7-23 (1978), Rodwell et al., *Biotech.*, 3:889-894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of an APC inhibitor of this invention in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in some embodiments, a PC polypeptide or a monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

The term "package" refers to a solid matrix or material such as glass, plastic (e.g., polyethylene, polypropylene and polycarbonate), paper, foil and the like capable of holding within fixed limits a diagnostic reagent such as a polypeptide, antibody or monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

E. Assay Methods

The present invention contemplates various assay methods for determining the presence, and preferably amount, of a serum protein susceptible to proteolysis by activated protein C (APC) in an aqueous composition such as a biological fluid sample where inhibition of APC is desirable to maintain the levels of the susceptible protein during the assay procedure. Typical serum proteins susceptible to inactivation by APC include Factor V, Factor Va, Factor VIII and Factor VIIIa, with the activated varieties being particularly susceptible to inactivation by APC.

Thus, the present invention contemplates an in vitro inactivation step in any assay method for determining the presence or amount of a serum protein that is inactivated by APC. Exemplary assay methods include the prothrombin time assay, the activated partial thromboplastin time (APTT) assay, the Factor Xa-1 stage assay, the Russell's viper venom clotting assay and the like assays dependent upon the presence of Factor Va or VIIIa. Particularly preferred are amidolytic assays using chromogenic substrates for determining the presence of the recited serum factors. These assay protocols are generally well known blood diagnostic assays, some of which are described in more full detail herein.

The diagnostic method of the present invention that utilizes an APC inhibitor comprises the step of contacting (admixing) one or more of the assay reaction mixtures (aqueous compositions) normally produced in the course of the diagnostic assay with an APC-inhibiting amount of an APC-inhibitor of this invention to inhibit the activity of APC and thereby prolong the stability of the susceptible serum protein to be detected during one or more manipulative steps of the assay procedure. Typically, the assay reaction admixture contains a buffer compatible with detection of the serum protein. Preferably, the APC inhibitor is admixed (contacted) with the fluid sample to be assayed at the earliest stages of the assay, and is preferably present in subsequent assay steps as well. At all steps in the diagnostic assay, it is preferred that an APC-inhibiting amount of an APC inhibitor of this invention is utilized. Thereafter, the presence, and preferably the amount, of the serum protein is measured according to the usual procedures for measuring the serum protein in the assay reaction mixture.

An APC-inhibiting amount of an APC inhibitor of this invention depends on the particular inhibitor to be utilized, e.g. a PC polypeptide or an anti-PC antibody of this invention, and also depends on the particular assay protocol to be utilized, as susceptibility to inactivation by APC can depend on the assay conditions including incubation times, temperature and the like. An APC-inhibiting amount is an amount sufficient to reduce the rate of inactivation of a susceptible serum protein to levels below background detection of the particular susceptible serum protein in the particular assay protocol. Exemplary amounts of APC inhibitor for use in the present in vitro APC inactivation-based assay methods can readily be determined using the methods are described in the Examples.

In another embodiment, the present invention contemplates various immunoassay methods for determining the presence, and preferably the amount, of an APC inhibitor of the present invention in a fluid sample using a polypeptide, polyclonal antibody or monoclonal antibody of this invention as an immunochemical reagent to form an immunoreaction product whose amount relates, either directly or indirectly, to the amount of the APC inhibitor in the sample. This embodiment is particularly useful to monitor the fate of therapeutically administered APC inhibitors as described in the therapeutic methods herein.

Those skilled in the art will understand that there are numerous well known clinical diagnostic chemistry procedures in which an immunochemical reagent of this invention can be used to form an immunoreaction product whose amount relates to the amount of APC inhibitor present in a body sample. Thus, while exemplary assay methods are described herein, the invention is not so limited.

Various heterogenous and homogeneous protocols, either competitive or noncompetitive, can be employed in performing an assay method of this invention. Typically, the present assay method comprises the steps of:

(a) Forming an immunoreaction admixture by admixing a vascular fluid sample with an anti-PC antibody of the present invention, preferably a monoclonal antibody, or a PC polypeptide of the present invention. Where the fluid sample contains a PC polypeptide, an anti-PC antibody immunospecific for the PC polypeptide is added to form the immunoreaction admixture. Where the fluid sample contains an anti-PC antibody, a PC polypeptide is added to form the immunoreaction admixture.

Preferably, the fluid sample is provided as a known amount of blood, or a blood derived product such as serum or plasma.

Preferably, the amount of antibody or PC polypeptide as immunochemical reagent that is admixed is known. Further preferred are embodiments where the antibody is labeled, i.e., operatively linked to an indicating means such as an enzyme, radionuclide and the like.

In preferred embodiments, the immunochemical reagent is present as part of a solid support, i.e., operatively linked to a solid matrix, so that the immunoreaction admixture formed has a solid and a liquid phase and the immunochemical reagent functions as a capture reagent. Further preferred are embodiments wherein the amount of polypeptide present in the immunoreaction admixture is an amount sufficient to form an excess of epitopes relative to the number of antibody combining sites present in the immunoreaction admixture capable of immunoreacting with those epitopes.

(b) The immunoreaction admixture is maintained under biological assay conditions for a predetermined time period such as about 10 minutes to about 16–20 hours at a temperature of about 4 degrees C. to about 45 degrees C. that, such time being sufficient for the APC inhibitor present in the sample to immunoreact with (immunologically bind) the immunochemical reagent to form an APC inhibitor-containing immunoreaction product (immunocomplex). In embodiments where the immunochemical reagent is in the solid phase, the immunocomplex formed is also present in the solid phase.

Biological assay conditions are those that maintain the biological activity of the immunochemical reagents of this invention and the APC inhibitor sought to be assayed. Those conditions include a temperature range of about 4 degrees C. to about 45 degrees C., a pH value range of about 5 to about 9 and an ionic strength varying from that of distilled water to that of about one molar sodium chloride. Methods for optimizing such conditions are well known in the art.

(c) The amount of APC inhibitor-containing immunoreaction product that formed in step (b) is determined, thereby determining the amount of APC inhibitor present in the sample.

Determining the amount of the APC inhibitor-containing immunoreaction product, either directly or indirectly, can be accomplished by assay techniques well known in the art, and typically depend on the type of indicating means used.

In preferred competitive assay methods, the amount of product determined in step (c) is related to the amount of immunoreaction product similarly formed and determined using a control sample in place of the vascular fluid sample, wherein the control sample contains a known amount of a subject polypeptide or antibody from which a standard curve is determined.

Exemplary of the contemplated diagnostic assay, wherein a PC polypeptide is operatively linked to a solid matrix is the ELISA described in Example 2.

Also contemplated are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

F. Factor V and Factor VIII Purification Method

The present invention also contemplates a method for purifying blood coagulation Factor VIII, Factor VIIIa, Factor V or Factor Va protein (also referred to collectively herein as Factor VIII or Factor V) from plasma or an aqueous solution derived therefrom. The method is based on the discovery herein of inhibitors of APC, and their demonstrated utility in in vitro inhibition of APC such as during the manipulative steps of a Factor V or Factor VIII purification protocol. The invention comprises the step of contacting (admixing) said plasma with an activated protein C (APC)-inhibiting amount of a composition comprising a PC polypeptide, antibody, or a monoclonal antibody of the present invention to form an APC inhibition admixture and then isolating (recovering) the Factor VIII and/or Factor V from said APC inhibition admixture to form purified Factor VIII or purified Factor V.

Methods for purifying Factor V and Factor VIII are well known in the art. See for example, U.S. Pat. No. Re. 32,011; EPO Publication No. 160,457; Vehar et al., *Biochem.*, 19:401-410 (1980); Dahlback et al., *J. Clin. Invest.*, 66:583-591 (1980); Suzuki et al., *J. Biol. Chem.*, 257:6556-6564 (1982) (incorporated herein by reference). Briefly, the plasma fraction is separated from the vascular fluid sample of a donor human or animal, and protease inhibitors are then added to the plasma to decrease inactivation of the desired Factors V or VIII by serine proteases present in the plasma fraction. The plasma fraction is subjected to barium citrate precipitation and further conventional purification steps such as PEG fractionation, ammonium sulfate precipitation and various gel chromatography and gel filtration techniques.

Sample preparations of Factor VIII or Factor V, such as human and animal plasmas and commercial concentrates of Factors VIII or V may be employed in the present invention and the method is not limited to a particular type of material. Preferred source materials for Factor V or Factor VIII are human, bovine or porcine plasmas and the commercial concentrate FACTORATE available from Armour Pharmaceutical Co.

As used herein, the phrase "contacting" refers to a variety of means which results in allowing the APC inhibitor, namely the PC polypeptide, antibody, or monoclonal antibody of the present invention, to come into contact with APC in the plasma under physiological conditions. Such means include, but are not limited to admixture of the APC inhibitor with the source of Factor V or Factor VIII to form an APC inhibition admixture comprising a liquid phase:liquid phase or solid matrix:liquid phase admixture, or by introduction of the APC inhibitor for contacting with the Factor V or Factor VIII by injection, infusion, implantation and the like into a donor prior to harvesting the plasma containing Factor V and/or Factor VIII.

The phrase "APC-inhibiting amount", refers to an amount of a PC polypeptide, antibody, or monoclonal antibody sufficient to measurably inhibit the APC activity present in the plasma or other source material for purifying Factor V or Factor VIII, preferably by at least about 10 percent, more preferably by at least about 50 percent and most preferably at least about 100 percent of the detectable APC activity. A contemplated dosage amount is within the range of about $10^{-7}$ molar to $10^{-2}$ molar PC polypeptide, and about 10 to 1000 nanomolar anti-PC antibody. The PC polypeptide, antibody or monoclonal antibody is typically administered as a pharmaceutical composition in the form of a solution or suspension. However, as is well known, a PC polypeptide, antibody, or monoclonal antibody either alone or in admixture, can also be formulated for therapeutic administration as a tablet, pill, capsule, aerosol, sustained release formulation or powder.

To improve the yields of Factor VIII and/or Factor V by contacting the plasma with an APC inhibiting amount of an APC inhibitor, the purification method typically includes forming an admixture by admixing an aqueous composition such as a vascular fluid sample containing Factor V or Factor VIII with an APC-inhibiting amount of an APC inhibitor of the present invention. The admixing can be performed prior to, or during, the barium citrate precipitation step of conventional protein purification methods previously described.

After admixture of the APC inhibitor of this invention to the aqueous composition containing the Factor V or Factor VIII to be purified, the conventional protein purification protocols are conducted for purifying either Factor V, Factor VIII, or both.

In a related embodiment, the present invention contemplates a method for purifying serum proteins normally susceptible to inactivation by APC. Such serum proteins include at least, Factor V, Factor Va, Factor VIII and Factor VIIIa, and are characterized by their capacity to by inactivated by the proteolytic cleavage activity of APC. Because these serum proteins are bound by APC as substrates for inactivation by cleavage, these same proteins can complex with the PC polypeptides of the present invention and form protein-PC polypeptide complexes.

Thus the present invention contemplates a method for purifying APC-inactivatable serum proteins by admixing an aqueous solution containing APC-inactivatable serum proteins with a solid support comprising a matrix having affixed thereto a PC polypeptide of the present invention to form a binding admixture having a liquid phase and a solid phase. The binding admixture is maintained for a time period and under binding conditions sufficient for any of the APC-inactivatable serum proteins in the aqueous solution to complex with the PC polypeptide in the solid phase and form a protein-PC polypeptide complex in the solid phase. Thereafter, the solid phase is separated from the liquid phase, and the bound protein is recovered from the solid phase thereby forming purified serum proteins.

In preferred embodiments, the solid phase protein-PC polypeptide complex is washed with buffers compatible with maintaining the complex formed in the solid phase, thereby rinsing excess liquid phase trapped in the matrix and associated with the solid phase. Thereafter, the solid phase is separated from the wash buffers and contacted with buffers formulated to perturb the protein-PC polypeptide complex and thereby release the bound protein from the solid support after a time period sufficient for release of the bound protein. After release of the bound protein into the liquid phase containing the release buffer, the liquid phase is recovered from the solid phase, thereby forming purified protein.

In one embodiment, the release buffer contains a polypeptide in the liquid phase that is the same polypeptide as is present in the solid phase to act as a competitor for binding of the protein to the solid phase. In another embodiment, the release buffer contains salts incompatible with the formation of a protein-PC polypeptide complex. Reagent conditions compatible with the binding reaction, with wash buffer, or with the release buffer can readily be developed by one skilled in the art using the assays and reagents described herein.

G. Therapeutic Compositions

The present invention contemplates therapeutic compositions useful for practicing the therapeutic methods described herein. Therapeutic compositions of the present invention contain a physiologically tolerable carrier together with an APC inhibitor, namely a PC polypeptide, an anti-PC antibody or monoclonal antibody as described herein, dissolved or dispersed therein as an active ingredient. In a preferred embodiment, the therapeutic APC inhibitor composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an APC-inhibiting amount of an APC inhibitor of the present invention, typically an amount of at least 0.1 weight percent of inhibitor per weight of total therapeutic composition. A weight percent is a ratio by weight of inhibitor to total composition. Thus, for example, 0.1 weight percent is 0.1 grams of inhibitor per 100 grams of total composition.

H. Therapeutic Methods

It has been discovered that the PC polypeptides, antibodies, and monoclonal antibodies of the present invention (i.e., APC inhibitors) have the capacity to inhibit APC. In view of APC's physiological role in inactivation of Factors Va and VIIIa, contributors to the coagulation of blood, inhibition of APC in vivo will increase the level of coagulation factors Va and VIIIa in a human patient and thereby promote coagulation. Stated differently, the inhibition of APC will reduce the anticoagulant effect of APC. The inactivation of Factors Va and VIIIa, where it occurs by the activity of APC, is referred to herein as "APC-mediated anticoagulation".

Thus, the present invention provides for a method for inhibiting vascular APC levels, and thereby increasing serum Factor Va and Factor VIIIa levels, in a patient comprising administering to the patient a therapeutically effective amount of a physiologically tolerable composition containing a PC polypeptide, antibody, or monoclonal antibody of the present invention.

A therapeutically effective amount of an APC inhibitor is a predetermined amount calculated to achieve the desired effect, i.e., to inhibit the in vivo APC activity present in a patient and thereby decrease the amount of APC-mediated anticoagulation occurring in the patient.

The in vivo inhibition of APC by an APC inhibitor of this invention is desirable in a variety of clinical settings, such as where the patient is exhibiting symptoms of bleeding that could be prevented by increases in vascular levels of Factor Va and/or Factor VIIIa. A particularly preferred clinical setting for in vivo inhibition of APC is during or after APC therapy when deleterious side effects of APC therapy are manifest by symptoms of bleeding tendency (diathesis) following APC or PC infusions. Typically, an APC therapy will be indicated when a patient exhibits disseminated intravascular coagulation (DIC), septic shock, venous or arterial thrombosis and the like conditions requiring anticoagulant intervention.

A therapeutically effective amount of a PC polypeptide of this invention is typically an amount of PC polypeptide such that when administered in a physiologically tolerable composition is sufficient to achieve a plasma concentration of from about 0.1 micromolar (uM) to about 100 uM, and preferably from about 0.5 uM to about 10 uM.

A therapeutically effective amount of an antibody of this invention is typically an amount of antibody such that when administered in a physiologically tolerable composition is sufficient to achieve a plasma concentration of from about 0.1 microgram (ug) per milliliter (ml) to about 100 ug/ml, preferably from about 1 ug/ml to about 5 ug/ml, and usually about 5 ug/ml.

The level of inhibition of APC present in a patient indicative of the efficacy of APC inhibition therapy can be readily determined by routine clinical analysis. Exemplary assays to monitor the level of APC and the level of inhibition of APC are described in Example 5a.

The therapeutic compositions containing an APC inhibitor of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of an PC polypeptide, antibody, or monoclonal antibody a diagnostic method of this invention for detecting a PC polypeptide, antibody, or monoclonal antibody, respectively, in the subject's blood is useful to characterize the fate of the administered therapeutic composition.

EXAMPLES

The following description provides details of the manner in which particular embodiments of the present invention may be made and used. This description, while exemplary of the present invention, is not to be construed as specifically limiting the invention. Variations and equivalents, now known or later developed, which would be within the understanding and technical competence of one skilled in this art are to be considered as falling within the scope of this invention.

1. Polypeptides

Overlapping synthetic protein C peptides from the heavy chain of protein C listed in Table 2 below were produced by the simultaneous multiple peptide synthesis method using the solid-phase technique described by Houghten, Proc. Natl. Acad. Sci. USA, 82:5131–5135 (1985). All peptides were synthesized in the carboxy-terminal amide form. The synthesized peptides were then analyzed by reverse phase high performance liquid chromatography (HPLC) on a Vydac C-18 column (Alltech Associates, Inc., Ill.) with a 0–60% acetonitrile linear gradient in 0.1% trifluoroacetic acid. Peptides were then purified to homogeneity by preparative HPLC using optimal conditions suggested by the analytical chromatography. In order to prevent disulfide formation among peptides, in some peptides the originally occurring cysteine was substituted by a serine or a glycine amino acid residue as indicated in Table 2. Amino acid compositions and concentrations of isolated peptides were determined by subjection to 24 hour hydrolysis in 6N HCl in evacuated tubes at 110 degrees Celsius (110° C.) and subsequent analysis on a Beckman Model 6300 High Performance Analyzer. Mass spectroscopic analyses of peptide-(390-404) (SEQ ID NO 1), -(317-331) (SEQ ID NO 1) and -(311-325) (SEQ ID NO 1) using the FIB positive ion mass spectra obtained on a VG-ZAB-VSE double focusing mass spectrometer equipped with a cesium ion gun yielded a single peak and the exact expected molecular weight of 1899 for the single protonated form of peptide-(390-404) (SEQ ID NO 1), 1721 for the single protonated form of peptide-(317-331) (SEQ ID NO 1) and 1845 for the single protonated form of peptide-(311-325) (SEQ ID NO 1).

Purified peptides were separately resuspended in distilled water to form a dissolved peptide solution at a final concentration of 2.5 mM. Subsequently, one-tenth volume of 10-fold concentrated buffer containing 0.05M Tris hydroxymethyl aminomethanehydrochloride (Tris-HCl) at pH 7.4 (TBS-Az) 0.1M sodium chloride (NaCl), 0.02% sodium azide (NaN$_3$). The pH of the solution was checked, and if necessary, adjusted to pH 7.4 with titrated amounts of 1M Tris-base. For peptides that appeared to be not completely soluble at 2.5 mM in TBS-Az, the partially dissolved peptide suspensions separately were centrifuged at 13,000×g to pellet the insoluble material. The molar concentrations in the resultant individual supernatants were estimated from the absorbance at 280 nm and 257 nm, respectively, for peptide solutions containing aromatic amino acids using a molar extinction coefficient of 5,600 $M^{-1}cm^{-1}$ for tryptophan and 1,400 $M^{-1}cm^{-1}$ for tyrosine at 280 nm, using a molar extinction coefficient of 200 $M^{-1}cm^{-1}$ for phenylalanine at 257 nm. Peptides without aromatic amino acids and poor solubility in aqueous solutions were not evaluated in this invention.

TABLE 2

| SEQ ID NO | RESIDUE* NUMBER | AMINO ACID SEQUENCE |
|---|---|---|
| (1) | 158-172 | DTEDQEDQVDPRLID |

TABLE 2-continued

| SEQ ID NO | RESIDUE* NUMBER | AMINO ACID SEQUENCE |
|---|---|---|
| (1) | 170-184 | LIDGKMTRRGDSPWQ |
| (1) | 176-190 | TRRGDSPWQVVLLDS |
| (5) | 188-202 | LDSKKKLA<u>S</u>GAVLIH |
| (6) | 202-216 | HPSWVLTAAH<u>S</u>MDES |
| (1) | 206-219 | VLTAAHCMDESKKL |
| (1) | 214-230 | DESKKLLVRLGEYDL |
| (1) | 216-230 | SKKLLVRLGEYDLRR |
| (1) | 224-238 | GEYDLRRWEKWELDL |
| (1) | 229-243 | RRWEKWELDLDIKEV |
| (1) | 235-249 | ELDLDIKEVFVHPNY |
| (1) | 239-253 | DIKEVFVHPNYSKST |
| (1) | 250-263 | SKSTTDNDIALLHLA |
| (1) | 260-274 | LLHLAQPATLSQTIV |
| (1) | 266-279 | PATLSQTIVPICLP |
| (7) | 266-280 | PATLSQTIVPI<u>S</u>LPD |
| (8) | 266-280 | PATLSQTIVPI<u>G</u>LPD |
| (1) | 273-287 | IVPI<u>S</u>LPDSGLAERE |
| (1) | 278-292 | LPD<u>S</u>GLAERELNQAG |
| (1) | 293-307 | QETLVTGWGYHSSRE |
| (1) | 303-317 | HSSREKEAKRNRTFV |
| (1) | 311-325 | KRNRTFVLNFIKIPV |
| (1) | 317-331 | VLNFIKIPVVPHNEC |
| (9) | 333-347 | EVMSNMVSENML<u>S</u>AG |
| (1) | 335-348 | MSNMVSENML<u>C</u>AGI |
| (1) | 346-355 | AGILGDRQDA |
| (10) | 351-365 | DRQDA<u>S</u>EGDSGGPMV |
| (1) | 353-366 | QDA<u>C</u>EGDSGGPMVA |
| (1) | 370-384 | GTWFLVLVSWGEGC |
| (3) | 384-398 | <u>S</u>GLLHNYGVYTKVSR |
| (1) | 390-404 | YGVYTKVSRYLDWIH |
| (11) | 404-390 | HIWDLYRSVKTYVGY |
| (4) | K395A-390-404 | YGVYTAVSRYLDWIH |
| (1) | 396-410 | VSRYLDWIHGHIRDK |
| (1) | 405-419 | GHIRDKEAPQKSWAP |

Underlined letters in the amino acid residue sequence indicate substitutions of originally occurring cysteines by either serine or glycine. For amino acid sequences labeled as SEQ ID NO 1, the residue number column indicates the position numbers of the peptide sequence with the heavy chain sequence of PC beginning with residue number 158 and ending with residue number 419 in SEQ ID NO 1.

2. Preparation of Polyclonal Antisera to Synthetic Polypeptides a. Preparation of Immunogen

For preparation of a peptide immunogen, the synthetic polypeptide-(390-404) (SEQ ID NO 1) was prepared as described in Example 1 but was modified with a carboxy-terminal cysteine. The synthesized peptide-(390-404) was coupled to keyhole-limpet-hemocyanin (KLH) (Sigma, St. Louis, Mo.) using the heterobifunctional crosslinking agent, N-succinimidyl-3-(2-pyridyldithio) propionate (SPDP)(Pierce Biochemicals, Rockford, Ill.). For the coupling procedure, 80 microliters ($\mu$l) of 10 mg/ml SPDP dissolved in dimethylformamide was admixed dropwise to 400 $\mu$l 15 mg/ml KLH in 0.1M phosphate, 0.1M NaCl at pH 8.5 under continuous stirring conditions for 30 minutes at 22° C. in order to form SPDP-activated KLH. The resultant SPDP-activated KLH was then extensively dialyzed at 4° C. against a buffered solution of 0.1M phosphate and 0.1M NaCl at pH 7.4 in order to remove uncoupled SPDP. Six mg of prepared peptide-(390-404) having a C-terminal cysteine was first dissolved in 2 ml of 0.1M phosphate and 0.1M NaCl at pH 7.4 and then admixed with SPDP-activated KLH prepared above under continuous stirring conditions. The degree of coupling of peptide-(390-404) with KLH was monitored by the pyridine-2-thione release at 343 nm ($\epsilon$: $8.08 \times 10^3$ $M^{-1}$ $cm^{-1}$) in a spectrophotometer.

b. Immunization and Collection of Polyclonal Antisera

The peptide-(390-404)-KLH immunogen prepared in Example 2a was emulsified using Adjuvant Complete Freund (DIFCO Laboratories, Detroit, Mich.) for the first injection and Adjuvant Incomplete Freund (DIFCO) for all subsequent injections according to the manufacturer's instructions, and the peptide-(390-404)-KLH antigens were incorporated into the emulsion at a concentration of 2 milligrams/milliliter (mg/ml). One-half ml of a prepared emulsion was injected subcutaneously into each of two New Zealand white rabbits after pre-immune serum samples were collected. The rabbits were injected three times at weekly intervals following the injection protocol as detailed. Two weeks after the last injection, blood samples were collected to check antibody titer against the specific peptide-(390-404) used as an immunogen by the ELISA assay described below. The collected blood samples were stored at 4° C. for 12 hours, after which the samples were centrifuged at 3000×g for 20 minutes. The resultant supernatant containing anti-peptide antibodies was collected and stored at −20° C.

Peptides-(176-190), -(239-253), -(311-325), -(317-331), -(384-398), -(396-410) and -K395A-(390-404) are also separately prepared as immunogens by conjugation with KLH as described in Example 2a. Immunization of separate rabbits for the production of antisera against each of the peptides listed above is performed as described herein. The resultant antisera are then screened by ELISA as described for anti-(390-404) antisera in Example 2c.

c. ELISA to Screen Antisera Immunoreactivity

The peptide antibody titers and immunospecificity in sera collected from rabbits in Example 2b were determined in an enzyme-linked-immunosorbent-assay (ELISA) as described below. The antigens used in the ELISA included the immunizing peptide-(390-404), human Protein C (PC) and activated Protein C (APC). The preparations of the latter two antigens are described below.

1) Preparation of Human PC

Human PC used was purified from plasma factor IX concentrate by affinity chromatography on a calcium-dependent, polyclonal, immunoaffinity-purified sheep anti-PC antibody column. The antibody affinity column was prepared by first obtaining the IgG fraction of polyclonal sheep anti-human-PC antibody. The polyclonal sheep anti-human PC antibody was obtained by subcutaneously immunizing sheep with purified human protein C in the presence of calcium following boosting procedures as described in Example 2b. Plasma from immunized sheep was obtained by plasmapheresis of citrate-anticoagulated blood and purification of the IgG fraction from the sheep plasma was achieved by ammonium-sulfate precipitation (50%) followed by purification of IgG on an ion-exchange DEAE Sephadex column (Pharmacia, Piscataway, N.J.). The resultant IgG fraction of polyclonal sheep anti-human PC antibody was further purified by column chromatography on a PC-Sepharose column. For preparing the PC-Sepharose column, human PC was first purified from plasma factor IX concentrate using immunoaffinity chromatography as follows. Anti-human PC light-chain monoclonal antibodies, designated C3, as described by Heeb et al., *Thrombosis Res.*, 52:33-43 (1988), were coupled to cyanogen-bromide (CNBr)-activated Sepharose 4B (Pharmacia) at a concentration of 3 mg protein to 1 ml gel in coupling buffer (0.5M NaCl and 0.05M borate at pH 8.5) overnight at 4.C to form a C3 antibody-Sepharose suspension. The suspension was packed into a column and washed with coupling buffer to remove unbound antibody according to manufacturer's instructions. Factor IX concentrate which was obtained from Dr. Hans Peter Schwarz, Immuno AG, Vienna, Austria, consisted of the following components in one gram (g) of bulk powder: protein-740 mg/g; sodium-citrate-47 mg/g; NaCl-77 mg/g; Factor II-1540 units/g; Factor IX-927 units/g; and Factor X-1119 units/g. The Factor IX was admixed with a buffer solution containing 0.1M NaCl, 2 mM ethylene diamine tetraacetic acid (EDTA), 2 mM benzamidine, 0.02% $NaN_3$, 0.02% Tween-20, 0.02M Tris-HCl at pH 7.4. The buffered Factor IX concentrate was then passed over the prepared C3-Sepharose antibody column to immobilize human PC on the antibody column and separate PC from non-PC contaminants. The antibody column containing immobilized PC was subsequently washed to further remove unbound proteins. Immobilized PC was then eluted from the column with 3M sodium thiocyanate (NaSCN) in 1.0M NaCl, 4 mM benzamidine, 2 mM EDTA, 0.02% $NaN_3$, 0.05% Tween-20 and 0.05M Tris-HCl at pH 7.0. The eluted and purified PC was determined to be greater than 95% pure when analyzed using sodium dodecyl sulfate-polyacrylamide gel electrophoresis (SDS-PAGE).

The purified human PC was then coupled to Sepharose 4B as described above to form an antigen column for purifying the IgG fraction of polyclonal sheep anti-human PC antibody described above. The sheep anti-human-PC antibody in TBS buffer at pH 7.4 containing 5 mM calcium chloride ($CaCl_2$) was admixed to the human PC-Sepharose column for immobilization of anti-PC specific antibodies. The calcium-dependent anti-PC antibodies immobilized on the PC-Sepharose column were then eluted with TBS containing 20 mM EDTA. The eluted anti-PC antibodies were dialyzed against a solution of 0.05M borate and 0.5M NaCl at pH 8.5. Twenty mg of dialyzed immunoaffinity-purified calcium-dependent sheep anti-human-PC IgG were then coupled to CNBr-activated Sepharose 4B as described above to form a human-PC antibody-Sepharose affinity column for purifying human PC for use in this invention. Protein C appeared as a single band with an apparent molecular weight of 62,000 daltons under non-reducing conditions. However, in the presence of a reducing agent, protein C formed two bands with mobilities representing 41,000 and 21,000 daltons. Human protein C, thus, consists of two polypeptide chains linked by a disulfide bond.

Human PC was then immunoaffinity-purified as previously described from plasma factor IX concentrate in TBS containing 5 mM $CaCl_2$ by immobilization on the calcium-dependent sheep anti-human PC-Sepharose column prepared above. The column containing immobilized PC was extensively washed with ten column volumes of a wash buffer at pH 7.4 consisting of 0.05M Tris-HCl, 1M NaCl, 5 mM $CaCl_2$, 0.02% $NaN_3$, 0.02% Tween 20 to remove contaminating unbound proteins. Immobilized human PC was subsequently eluted with 0.05M Tris-HCl, 1M NaCl, 20 mM EDTA at pH 7.4. The purification of human PC from plasma factor IX concentrate was repeated several times yielding approximately 3.6 mg PC each time without significant loss of capacity of the anti-PC column. The separate elutions of purified human PC were pooled and subsequently dialyzed against five liters with four changes of TBS as described above to remove excess salts. The resultant purified human PC in its inactive or zymogen form was then used in ELISA as described below.

2) Preparation of Activated PC

The activated form of PC (APC) was prepared by treating the inactive zymogen PC prepared above with soluble alpha-thrombin-Sepharose beads. Thrombin was purchased from Enzyme Research Laboratories (South Bend, Ind.) and prepared from homogeneous human prothrombin by activation with Factor Xa, Factor Va and phospholipid. Human thrombin was homogeneous as judged by 10% SDS-PAGE. The purified thrombin was coupled to CNBr-activated Sepharose as described above. To monitor the activation of protein C, the amidolytic activity was determined in an assay using the chromogenic substrate, S-2238 (H-D-Phenylalanyl-L-pipecolyl-L-arginine-p-nitroanilide dihydrochloride, Kabi-Vitrum, Franklin, Ohio). In the assay, 60 µl of the sample was admixed to 600 µl of 0.8 mM amidolytic substrate in a buffer consisting of 0.05M Tris-HCl and 0.10M NaCl at pH 8.0. The rate of absorbance change at a wavelength of 405 nm/minute was determined. The resultant APC product was determined to be greater than 95% pure when analyzed by SDS-PAGE as described above.

3) Preparation of Antigen-Coated ELISA Plates and Detection of Immunoreactive Products To determine the immunospecificity of the rabbit antisera obtained in Example 2b, ELISA assays were performed. Briefly, 50 µl of either 50 µM peptide-(390-404) prepared in Example 1 or 10 µg/ml of PC or APC prepared in Example 2c in a buffer consisting of 0.05M sodium carbonate ($Na_2CO_3$) and 0.02% $NaN_3$ at pH 9.0 were admixed into the wells of microtiter plates. The plates were maintained at 37° C. for one hour to permit the antigens to become operatively affixed to the well walls. After washing the antigen-coated wells with TBS, the wells were blocked with 250 µl/well of 10% bovine serum albumin (BSA) (Sigma) in TBS for one hour at 22° C. The blocking solution was then removed and the wells were subsequently washed five times with 250 µl/well of maintenance buffer (0.05M Tris-HCl, 0.1M NaCl, 0.02% $NaN_3$, 1 mg/ml BSA, 5 mM $CaCl_2$, 0.01% Tween 20 at pH 7.4). Fifty µl of rabbit non-immune or specific antiserum serially diluted in maintenance buffer was then admixed to the washed wells and maintained for one hour at 37° C. to allow formation of a solid liquid phase immunoreaction products. The wells were then washed three times with maintenance buffer followed by admixture of 50 µl of 2.0 µg/ml of secondary antibody (polyclonal biotinylated goat-anti-rabbit-IgG) (Pierce Biochemicals) diluted in maintenance buffer to each well for the detection of immunoreactant products. The plates were maintained for 1 hour at 37° C. after which time the secondary antibody solution was removed. After washing the wells as described above, 50 µl of 2.0 µg/ml streptavidin-alkaline-phosphatase (Pierce Biochemicals) in maintenance buffer was admixed into each well and maintained for 30 minutes at 37° C. Detection of specific immunoreaction products was obtained by admixture of 150 µl/well of 5 mg/ml p-nitrophenylphosphate (PNPP) (Pierce Biochemicals) in 0.1M diethanolamine and 0.02% NaN$_3$ at pH 9.6 followed by measurement of the change in absorbance at 405 nm over time using the EL312 Microplate Bio-Kinetics Reader and the KinetiCalc Software Program (Biotek Instruments, Inc., Vt.). Non-specific binding was considered as the measured absorbance in 10% BSA blocked wells which served as negative controls without the preceding coating of a specific protein or peptide. Under the described conditions, non-specific binding never exceeded more than 5% of the specific binding. Rabbit antisera which exhibited significant immunoreactivity as compared to the pre-immune serum toward peptide-(390-404), PC and APC was selected for further purification as described in Example 3.

Rabbit antisera which are obtained in Example 2b against peptides -(176-190), -(239-253), -(311-325), -(317-331), -(384-398), -(396-410), and -K395A-(390-404) are screened for immunoreactivity to the respective peptide immunogens and PC or APC as described above. Rabbit antisera which exhibit significant immunoreactivity as compared to the pre-immune serums toward the peptide immunogen and PC and APC are further purified and analyzed as described in Example 3.

3. Purification of Anti-PC Antibody, Anti-(390-404)

Purification of the IgG fraction from rabbit antiserum, which showed significant reactivity towards peptide-(390-404), was achieved by ammonium-sulfate precipitation (0–45%), followed by purification of IgG on an ion-exchange Mono Q column (Pharmacia) connected to a fast protein liquid chromatography (FPLC) system (Pharmacia). Immunoaffinity purification of the pooled immunoreactive IgG-fraction was performed by passing the IgG over a 3-ml column of protein C prepared in Example 2a (3.4 mg of immunoaffinity-purified PC/ml gel) coupled to Sepharose 4B (Pharmacia) as described in Example 2a. After thorough washing of the column with 5 column volumes of 0.05M Tris-HCl and 1M NaCl at pH 7.4 to remove unbound antibodies, the bound IgG was eluted with two column volumes of 0.1M glycine-HCl at pH 2.5. The eluted protein was monitored by absorbance at 280 nm and the IgG concentrations determined from the extinction coefficient of 13.5. The eluted IgG was immediately dialyzed against TBS-Az, concentrated against 50% sucrose and once more extensively dialyzed against TBS-Az. Analysis by 4–15% SDS-PAGE of reduced and non-reduced samples revealed greater than 95% pure IgG. This immunoaffinity-purified anti-peptide antibody is designated anti-(390-404) for use in this invention.

a. Specificity and Affinity Analysis of Anti-(390-404)

The specificity of immunoaffinity purified anti-(390-404) antibody towards peptide-(390-404) and PC was evaluated by measuring the binding in solid-phase ELISA of the antibody to immobilized peptides including -(384-398), -(390-404), -(396-410), -(404-390), and -K395A-(390-404) listed in Table 1 with their corresponding SEQ ID NO, and to PC. For the ELISA assay, 50 µM of each peptide and 10 µg/ml of PC protein were admixed into separate wells of microtiter plates as described in Example 2c. After blocking the peptide- or protein-coated wells as described in Example 2c, 50 µl of 2 µg/ml immunoaffinity purified anti-(390-404) antibody in maintenance buffer were admixed into each well and maintained for one hour at 37° C. to form an immunoreaction product. The detection and measurement of specific immunoreaction products was accomplished by admixture of streptavidin-alkaline-phosphatase followed by PNPP as described previously for the ELISA in Example 2c.

The results of the ELISA are shown in Table 3 below. The data represent the mean values of duplicate measurements. Negative controls revealed less than 5% non-specific binding. The anti-(390-404) antibody specifically recognized immobilized peptide-(390-404) but did not bind significantly to peptides-(384-398), -(396-410) or -(404-390). Fifteen percent binding of anti-(390-404) antibody to peptide-K395A-(390-404), in which amino acid residue Lysine at position 395 had been changed to Alanine, was exhibited compared to binding to peptide -(390-404). Significant immunoreactivity was observed between PC and anti-(390-404) antibody. In additional experiments, the immunoaffinity-purified polyclonal anti-(390-404) antibody bound to immobilized PC as well as to APC in a saturable manner with the same affinity.

TABLE 3

| Protein or Peptide | SEQ ID NO | Anti-(390-404) (Absorbance/20 min.) |
|---|---|---|
| Protein C | | 249 |
| -(390-404) | (1) | 493 |
| -K395A-(390-404) | (4) | 66 |
| -(384-398) | (1) | 3 |
| -(396-410) | (1) 69 | 3 |
| -(404-390) | (11) | 5 |

The specificity of anti-(390-404) antibody for peptide-(390-404) and PC was confirmed by cross-competition binding experiments. The binding assays were performed by first admixing separate aliquots of 2 µg/ml anti-(390-404) with either 0–200 µg/ml of either PC, or 0 to 1 mM peptide-(390-404), -(404-390) or 0 to 0.2 mM peptide-K395A-(390-404) in maintenance buffer prepared as described in Example 2c for 30 minutes at 37.C prior to admixture to microtiter wells previously coated with 10 µg/ml of PC to form immobilized PC as described in Example 2c. The remainder of the assay was performed as described for ELISA above and in Example 2c. Bound anti-(390-404) antibody to immobilized PC in the presence of competitors was detected as described in Example 2c.

The results of the cross-competition experiments are shown in FIG. 1 where the amount of anti-(390-404) antibody which specifically bound to PC-coated wells in the absence of any competing protein was defined as 100%. Only PC and peptide-(390-404) competed significantly with the binding of anti-(390-404) antibody to immobilized PC compared to the other peptides evaluated in the assay. Half-maximal inhibition of anti-(390-404) antibody binding to immobilized PC occurred at about 9.2 nM PC and 4.4 µM peptide-(390-404) in fluid-phase. These data suggest that about one out of 500 peptide molecules at a certain time point is in an appropriate conformation capable to compete with native PC for binding to anti-(390-404) antibody.

The affinity of immunoaffinity purified anti-(390-404) antibody towards APC was determined by Scatchard-analysis. Fifty µl of anti-(390-404) antibody diluted to a concentration of 10 µg/ml in 0.05M Na$_2$CO$_3$ and 0.02% NaN$_3$ at pH 9.0 were admixed to wells of a microtiter plate and maintained for one hour at 37° C. to form antibody-coated wells. Following the removal of the antibody solution at the end of the maintenance period, 250 μl of 10% BSA in TBS-Az at pH 7.4 was admixed into each well for one hour at 22° C. to block unoccupied sites on the wells. For wells which were used as negative controls, the antibody coating step was omitted prior to the blocking step. The antibody-coated and blocked wells were then washed three times with maintenance buffer prepared as described in Example 2c. Fifty μl of APC prepared as described in Example 2a diluted in maintenance buffer to concentrations ranging from 0 to 1.2 μg/ml were admixed into the washed wells and maintained for one hour at 37° C. to form an immunoreaction product. The wells were subsequently washed five times with maintenance buffer. APC which bound to anti-(390-404) antibody was detected by the admixture of 100 μl of 0.8 mM of the chromogenic substrate, S-2366, (L-pyroglutamyl-L-prolyl-L-arginine-p-nitroanilide hydrochloride; Kabi-Vitrum) diluted in TBS-Az and 0.1% BSA at pH 8.0. The APC-amidolytic activity was monitored by the change in absorbance at 405 nm using the EL312 Microplate Reader. The amount of bound APC to immobilized anti-(390-404) antibody was calculated from a standard curve based on the amidolytic activity of known amounts of APC in fluid-phase.

Figure 2:
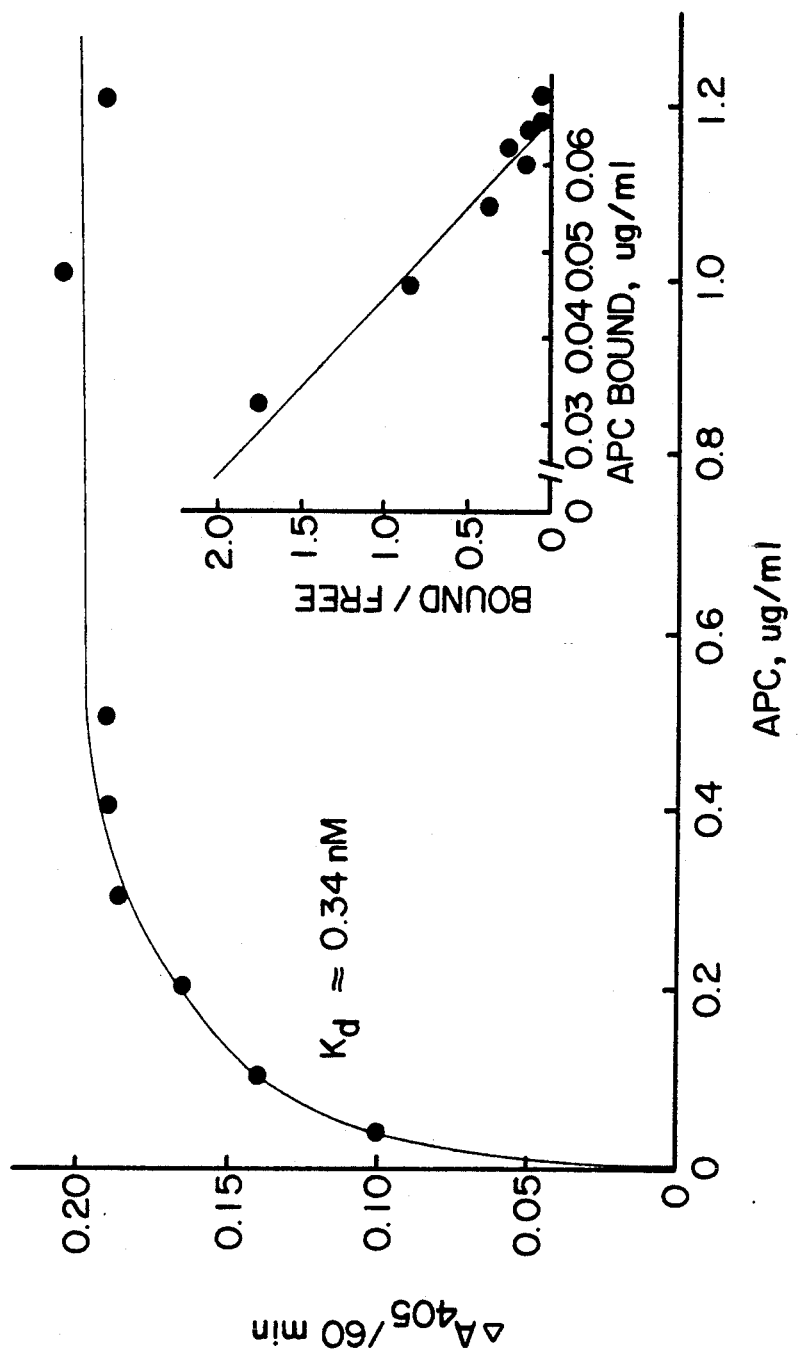
FIG. 2 illustrates the binding of activated Protein C (APC) to immobilized anti-(390-404) antibody. Ten $\mu$g/ml of anti-(390-404) antibody were coated on microtiter wells. After blocking with 10% BSA, wells were maintained with 0 to 1.2 $\mu$g/ml APC. Following a washing step to remove unbound APC, bound APC was detected by the addition of S-2366 as described in Example 2c and the change in absorbance at 405 nm was measured over time. Scatchard-analysis of the data using known amounts of APC in fluid-phase as standards yielded a single class of binding sites with a dissociation-constant ($K_d$) of 0.34 nM as depicted in the inset figure. Linear regression analysis for data in the inset yielded a correlation of (r) of $-0.979$. All plotted data are mean values of duplicate measurements.

The results of the Scatchard-analysis of the change in absorbance measured above, using known amounts of APC in fluid-phase as standards, yielded a single class of binding sites with a dissociation constant ($K_d$) of 0.34 nM as shown in FIG. 2. This result indicates that a homogeneous population of antibodies with the same apparent $K_d$ was produced. Linear regression analysis for data in the inset figure in FIG. 2 yielded a correlation (r) of $-0.979$. The plotted data represent the mean values of duplicate measurements. The binding of the anti-(390-404) antibody to PC or APC was not dependent on the presence of calcium, since in the absence of $CaCl_2$ but in the presence of 100 μM of the calcium chelator, EDTA, the same degree of binding was observed.

Thus, polyclonal antibodies raised against the most potent inhibitory peptide-(390-404), as described in Example 5 that were immunoaffinity-purified on a PC-Sepharose column, indicated that at least parts of the region represented by this peptide in PC were exposed and available for interaction with other molecular species at the solvent-accessible surface of PC. Antibodies produced against small synthetic peptides have been shown to be capable of recognizing native protein. The immunoaffinity-purified anti-peptide-(390-404) antibody recognized PC as well as APC with an apparent dissociation constant ($K_d$) of 0.34 nM and a single class of binding sites (FIG. 2). Anti-(390-404) antibody specifically recognized the sequence of peptide-(390-404) but did not significantly bind to peptide-(404-390), -(384-398) or -(396-410) (Table 3). Thus, the epitope for anti-(390-404) resides in the peptide sequence comprising residues 390-404. Polyclonal antibodies to short synthetic peptides recognize a limited number of epitopes within a peptide; the epitope recognized by a polyclonal antibody to a synthetic peptide can be as small as four amino acid residues and smaller than the epitope recognized by a monoclonal antibody raised to the same peptide. Thus, anti-peptide antibodies to short peptides share some functional characteristics with a monoclonal antibody. This is suggested in the case of anti-(390-404) since Scatchard-analysis indicated a single class of binding sites on APC (FIG. 2).

4. Preparation of Monoclonal Antibodies a. Anti-peptide

The polypeptide designated -(390-404) is prepared as an immunogen according to Example 2a. Balb/c ByJ mice (Scripps Clinic and Research Foundation Vivarium, La Jolla, Calif.) are immunized intraperitoneally (i.p.) with 50 μg of prepared peptide-(390-404)-KLH immunogen in complete Freund's adjuvant (CFA) followed by a second and third immunization using the same peptide-(390-404)-KLH immunogen, each about three weeks apart, in incomplete Freund's adjuvant (IFA). The mice receive a boost of 50 μg of the prepared peptide intravenously (i.v.) in normal saline 4 days prior to fusion and a second similar perfusion boost one day later.

The animals so treated are sacrificed and the spleen of each mouse was harvested. A spleen cell suspension is then prepared. Spleen cells are then extracted from the spleen cell suspension by centrifugation for about 10 minutes at 1000 r.p.m., at 23° C. Following removal of the resultant supernatant, the cell pellet is resuspended in 5 ml cold ammonium chloride ($NH_4Cl$) lysing buffer, and is maintained for about 10 minutes.

Ten ml of Dulbecco's Modified Eagle Medium (DMEM) (GIBCO) and HEPES [4-(2-hydroxyethyl)-1-piperidineethanesulfonic acid] buffer are admixed to the lysed cell suspension to form an admixture, and that admixture is centrifuged for about 10 minutes at 1000 r.p.m. at 23° C.

After the resultant supernatant is decanted, the pellet is resuspended in 15 ml of DMEM and HEPES and is centrifuged for about 10 minutes at 1000 r.p.m. at 23° C. The above procedure is repeated.

The pellet is then resuspended in 5 ml DMEM and HEPES. An aliquot of the spleen cell suspension is then removed for counting. Fusions are accomplished in the following manner using the non-secreting mouse myeloma cell line P3X63Ag 8.653.1, a subclone of line P3x63Ag 8.653 (ATCC 1580). With a myeloma to spleen cell ratio of about 1 to 10 or about 1 to 5, a sufficient quantity of myeloma cells are centrifuged into a pellet, washed twice in 15 ml DMEM and HEPES, and then centrifuged for 10 minutes at 1000 r.p.m. at 23° C.

Spleen cells and myeloma cells are combined in round bottom 15 ml tubes. The cell mixture is centrifuged for 10 minutes at 1000 r.p.m. at 23° C. and the supernatant is removed by aspiration. Thereafter, 200 μl of 50 percent (weight per volume) aqueous polyethylene glycol 4000 molecular weight (PEG); (ATCC Baltimore, Md.) at about 37° C. are admixed with the pellet using a 1 ml pipette with vigorous stirring to disrupt the pellet. The cells are then gently mixed for between 15 and 30 seconds. The resultant cell mixture is centrifuged 4 minutes at 700 r.p.m.

At about 8 minutes for the time of adding the PEG, 5 ml of DMEM plus HEPES buffer are admixed slowly to the pellet, without disturbing the cells. After 1 minute, the resulting admixture is broken up with a 1 ml pipette and is maintained for an additional 4 minutes. This admixture is centrifuged for 7 minutes at 1000 r.p.m. The resultant supernatant is decanted, 5 ml of HT (hypoxanthine/thymidine) medium are slowly admixed to the pellet, and the admixture is maintained undisturbed for 5 minutes. The pellet is then broken into large chunks and the final cell suspension is placed into T75 flasks (2.5 ml per flask) into which 7.5 ml HT medium have been placed previously. The resulting cell suspension is maintained at 37° C. to grow the fused cells. After 24½ hours 10 ml of HT medium are admixed to the flasks followed 6 hours later by admixture of 0.3 ml of 0.04 mM aminopterin. Forty-eight hours after fusion, 10 ml of HAT (hypoxanthine/aminopterin/-thymidine) medium are admixed to the flasks.

Three days after fusion, viable cells are plated out in 96-well tissue culture plates at about $2\times10^4$ viable cells per well (768 total wells) in HAT buffer medium as described in Kennett et al., *Curr. Top. Microbiol. Immunol.*, 81:77 (1978). The cells are fed seven days after fusion with HAT medium and at approximately 4–5 day intervals thereafter as needed with HT medium. Growth is followed microscopically and culture supernatants are collected about two weeks later. The culture supernatants are subsequently assayed for the presence of peptide-(390-404) specific antibody by solid-phase ELISA as described in Example 2c or by solid-phase radioimmunoassay (RIA) described below.

For screening by RIA, 50 μl of PBS containing 5 μg/ml of the prepared peptide-(390-404)-KLH immunogen is admixed into the wells of microtiter plates. The plates are maintained overnight (about 16 hours) at 4° C. to permit the peptide-(390-404)-KLH immunogen to adhere to well walls. After washing the wells four times with SPRIA buffer (2.68 mM potassium chloride (KCl), 1.47 mM potassium phosphate ($KH_2PO_4$), 137 mM NaCl, 8.03 mM sodium phosphate ($Na_2HPO_4$), 0.05% Tween-20, 0.1 KIU/ml Traysol, 0.1% BSA, 0.015% $NaN_3$), 200 μl of SPRIA buffer containing 3% normal goat serum and 3% BSA are admixed to each well to block excess protein binding sites. The plates are maintained for 30 minutes at 20° C., the wells emptied by shaking, and subsequently blotted dry to form a solid-support, i.e., a solid matrix to which peptide-(390-404)-KLH immunogen is operatively affixed.

To each well is then admixed 50 μl of hybridoma tissue culture supernatant to form a solid-liquid phase immunoreaction admixture. The admixture is maintained for 2 hours at 37° C. to permit formation of solid-phase immunoreaction products. After washing the wells as previously described, 50 μl of $^{125}I$-labeled goat anti-mouse IgG at 0.25 μg protein per ml are admixed to each well to form a labeling reaction admixture. That admixture is maintained for 1 hour at 37° C. to permit formation of $^{125}I$-labeled solid-phase immunoreaction products. After washing the wells as previously described, the amount of $^{125}I$-labeled product bound to each well is determined by gamma scintillation.

Hybridomas are selected from hybridoma cultures that secrete anti-peptide-(390-404) antibodies into their culture media, and further characterized as described herein.

Monoclonal antibodies are also raised against the following peptide immunogens coupled to KLH as described above for peptide-(390-404): peptides-(176-190), -(239-253); -(311-325); -(317-331); -(384-398); -(396-410); and -K395A-(390-404). The produced monoclonal antibodies are purified as described below.

b. Purification of Monoclonal Antibody

Ascites fluids are obtained from separate sets of 10-week old Balb/c mice, which are primed with 0.3 ml of mineral oil and injected intraperitoneally with $5\times10^6$ hybridoma cells prepared above. The average time for development of ascites is 9 days. Following clarification by centrifugation at 15,000×g for 15 minutes at 23° C., ascites fluids produced by hybridomas are pooled and stored frozen at −20° C.

Purified monoclonal antibodies directed against peptide-(390-404)-KLH from the hybridomas are prepared by fast protein liquid chromatography (FPLC) using a Pharmacia Mono Q HR5/5 anion exchange column (Pharmacia) using a 0–0.5M NaCl gradient in 10 mM Tris-HCl at pH 8.0 following directions supplied with the column. Purified Mabs were concentrated using an Amicon stirred ultrafiltration cell (Danvers, Mass.; PM 30 membrane) to a concentration of 1 mg/ml, dialyzed into PBS (phosphate-buffered saline at pH 7.2) and stored at −70° C.

Hybridomas secreting anti-peptide-(390-404) antibodies as described in Example 4A are injected into 10-week old Balb/c mice as described above to obtain ascites fluid. Purified anti-peptide-(390-404) monoclonal antibodies are prepared by FPLC and are concentrated in an Amicon stirred ultrafiltration cell and stored as described.

5. Inhibition of APC a. Inhibition of APC by Synthetic Peptides Derived from PC

The 32 overlapping PC peptides derived from the heavy chain of the zymogen PC were screened for their ability to inhibit APC anticoagulant activity in five different assays as described below. The peptides evaluated in the assays are listed in Table 2 according to the corresponding region in the PC heavy chain and by their SEQ ID NO. Hereinafter, the peptides will be referred to by the corresponding region in PC, e.g., peptide-(390-404). The assays were used to determine the region in APC essential for the protein's anticoagulant activity and for the recognition of the macromolecular substrates, activated Factors V (Va) and VIII (VIIIa).

1) Activated Partial Thromboplastin Time (APTT) Coagulation Assay

The effect of the synthetic peptides on APC anticoagulant activity were determined using the APTT assay in the presence of either normal citrate anticoagulated plasma (NHP) or protein S depleted plasma (PSDP). The assays were performed essentially as described. See Marlar et al., *Blood*, 59:1067–1072 (1082); Suzuki et al., *J. Biol. Chem.*, 258:163–168 (1983); Gruber et al., *Blood*, 73:639–642 (1989); Ohlin et al., *Biochem.*, 29:644–651 (1990). NHP was purchased from George King Bio-Medical, Inc. (Overland Park, Kans.). PSDP was prepared from a normal human citrate-anticoagulated plasma pool from ten healthy donors. Protein S was immunodepleted from the NHP by immunoaffinity chromatography of NHP over an anti-protein S antibody column to form PSDP. The anti-protein S antibody column was prepared by coupling 100 mg of a monoclonal, high-affinity, calcium-independent anti-PS antibody, designated S7, to 30 ml of CNBr-activated Sepharose 4B (Pharmacia) as described in Example 2c1). Residual total protein S content in the resultant PSDP was less than 0.1% protein S as determined by quantitative immunoblotting, by solid-phase ELISA for total protein S and by electroimmunoassay.

For the APTT assay, APC was prepared as described in Example 2c2). The specific anticoagulant activity of APC was determined to be 250 Units/mg. The concentration of the APC used in the assay was initially optimized with respect to the sensitivity of the assay towards APC-induced prolongation of clotting time compared to clotting time without APC.

Once the optimal concentration of APC was determined, peptides from Table 2 were then separately admixed for a final concentration of 500 $\mu$M with 10 nM APC in 100 $\mu$l of TBS-BSA at pH 7.4 to form peptide-APC admixtures. The resulting admixtures were maintained for seven minutes at 37° C. Separate aliquots of peptides maintained under the same conditions in the absence of APC served as controls for the inhibitory effect of synthetic peptides on APC anticoagulant activity. After the maintenance period, 100 $\mu$l of NHP and 100 $\mu$l APTT-reagent Thrombosil (Ortho Diagnostics, Raritan, N.J.) were admixed into each peptide admixture and maintained for 200 seconds at 37° C. to form a pre-coagulation admixture. In some experiments, PSDP was used in the place of NHP to determine the effect of Protein S on the assay system. Coagulation was then initiated by the admixture of 100 $\mu$l of 30 mM CaCl$_2$ in TBS prewarmed to 37° C. to each of the pre-coagulation admixtures. The time for clot formation was measured by an Electra 700 Automatic Coagulation Timer (Medical Laboratory Automation, Inc., Mount Vernon, N.Y.). Each peptide's effect was determined in duplicate.

Table 4 summarizes the percentage of inhibition of APC activity calculated from the APC standard curve. The synthetic peptides listed in Table 4 are presented in the same order as listed in Table 2, i.e., are reproduced from Table 2. APC anticoagulant activity standard curves were generated for each experimental series wherein a straight line resulted when APC-induced prolongation of clotting time was plotted against APC-concentration on a double-logarithmic plot. The standard curves were constant with a deviation of 6% over the course of the experiment. The mean values from the APTT assay and the Xa-1 stage assay described in Example 5a2) are displayed in Table 4 with peptides used at a final concentration of 500 $\mu$M since no significant difference in the inhibition of APC activity was obtained between either assay evaluated. For peptides at a concentration of 500 $\mu$M that inhibited at least 50% of APC anticoagulant activity, analysis of dose-response was subsequently conducted. The column in Table 4 labeled "Inhibition of APC" represents the inhibition of APC anticoagulant activity measured with 500 $\mu$M peptide. The peptide concentrations at which 50% and 90% inhibition of APC activity were observed were designated IC$_{50}$ and IC$_{90}$ values, respectively.

TABLE 4

| SEQ ID NO | Inhibition of APC (%) | IC$_{50}$ ($\mu$M) | IC$_{90}$** ($\mu$M) |
|---|---|---|---|
| (1) | 0 | — | — |
| (1) | 0 | — | — |
| (1) | 25 | — | — |
| (5) | 0 | — | — |
| (6) | 0 | — | — |
| (1) | 0 | — | — |
| (1) | 0 | — | — |
| (1) | 0 | — | — |
| (1) | 0 | — | — |
| (1) | 0 | — | — |
| (1) | 0 | — | — |
| (1) | 20 | — | — |
| (1) | 0 | — | — |
| (1) | 0 | — | — |
| (1) | 0 | — | — |
| (7) | 0 | — | — |
| (8) | 0 | — | — |
| (1) | 0 | — | — |
| (1) | 0 | — | — |
| (1) | 0 | — | — |
| (1) | 0 | — | — |
| (1) | nt | 20 | 50# |
| (1) | 50 | 500 | — |
| (9) | 0 | — | — |
| (1) | 0 | — | — |
| (1) | 0 | — | — |
| (10) | 0 | — | — |
| (1) | 0 | — | — |
| (1) | 0 | — | — |
| (3) | 60 | 425 | >500 |
| (1) | 100 | 5 | 40 |
| (11) | 0 | 0 | 0 |
| (4) | 23* | — | — |
| (1) | 95 | 70 | 300 |
| (1) | 0 | — | — |

0 is defined as no observable effect ± 10%
*measured at 36 $\mu$M peptide
**IC$_{50}$ and IC$_{90}$ values indicate the final peptide concentrations in $\mu$M at which 50 and 90% inhibition of APC activity could be observed
— means not tested
no effect on APC in Xa-1-stage assay up to 100 $\mu$M (peptide-(311-325))

Five synthetic peptides significantly and dose-dependently inhibited APC anticoagulant activity when APTT assays were performed in the presence of APC as shown in Table 4. The five are listed in the following descending order of potency:

peptide-(390-404): IC$_{50}$ of 5 $\mu$M and IC$_{90}$ of 40 $\mu$M;
peptide-(311-325); IC$_{50}$ of 20 $\mu$M and IC$_{90}$ of 50 $\mu$M;
peptide-(396-410): IC$_{50}$ of 70 $\mu$M and IC$_{90}$ of 300 $\mu$M;
peptide-(384-398): IC$_{50}$ of 425 $\mu$M; and
peptide-(317-331): IC$_{50}$ of 500 $\mu$M.

The peptide-K395A-(390-404), in which a specific Lysine to Alanine amino acid residue substitution has been made, inhibited only 23% of APC anticoagulant activity at 36 $\mu$M peptide concentration. Higher concentrations of this peptide could not be evaluated due to limitations of solubility in buffer solutions. The reverse sequence to the most effective peptide, designated peptide-(404-390), failed to inhibit APC anticoagulant activity. Peptide-(390-404) was, therefore, the most potent inhibitor of APC anticoagulant activity.

2) Xa-1-Stage Coagulation Assay

For testing the inhibition of the synthetic peptides on APC activity described above, Xa-1-stage coagulation assays were also performed as described. See Seegers et al., *Thrombosis Res.*, 13:233–243 (1978); Marlar et al., supra; and Walker et al., *J. Biol. Chem.* 265:1484–1489 (1990). Peptides from Table 2 were prepared as described above and separately admixed for a final concentration of 2 mM with 120 nM APC in 100 $\mu$l of TBS-BSA at pH 7.4 to form separate peptide-APC admixtures. The resulting admixtures were maintained for seven minutes at 37° C. Separate aliquots of peptides maintained under the same conditions in the absence of APC served as controls for the inhibitory effect of synthetic peptides on APC anticoagulant activity. After the maintenance period, 100 $\mu$l of NHP and 100 $\mu$l of 200 $\mu$g/ml of rabbit brain cephalin (Sigma) were admixed into each peptide admixture and maintained for 200 seconds at 37° C. to form pre-coagulation admixtures. In some experiments, Factor VIII deficient plasma (George King Bio-Medical, Inc.) was used in the place of NHP to determine the effect of Factor VIII on the assay system. Coagulation was then initiated by the admixture of 100 μl of 0.62 nM human activated Factor X (Xa) (Enzyme Research Laboratories, Southbend, Ind.) in TBS-BSA containing 30 mM CaCl₂ prewarmed to 37° C. to each of the pre-coagulation admixtures.

The time for clot formation was measured by an Electra 700 Automatic Coagulation Timer (Medical Laboratory Automation, Inc., Mount Vernon, N.Y.). Each peptide's effect was determined in duplicate. The results of the inhibition of APC anticoagulant activity by synthetic peptides as measured in Xa-1-stage coagulation assays are described above and are presented as the mean values obtained with APTT assays.

Additional assays were performed to compare the specificity of the inhibitory effect of peptide-(390-404) on APC anticoagulant activity. Both APTT and Xa-1-stage assays were performed with peptide-(390-404) and with the same peptide synthesized in the reverse order, peptide-(404-390), at concentrations of the peptides ranging from 0 μM to 40 μM. In APTT assays performed as described above in the presence of NHP, APC was used at a concentration of 2.5 nM. For APTT assays in the presence of PSDP, APC was used at a concentration of 5 nM. In the Xa-1-stage assays performed in the presence of factor VIII deficient plasma, APC was used at a concentration of 30.0 nM.

Figure 3:
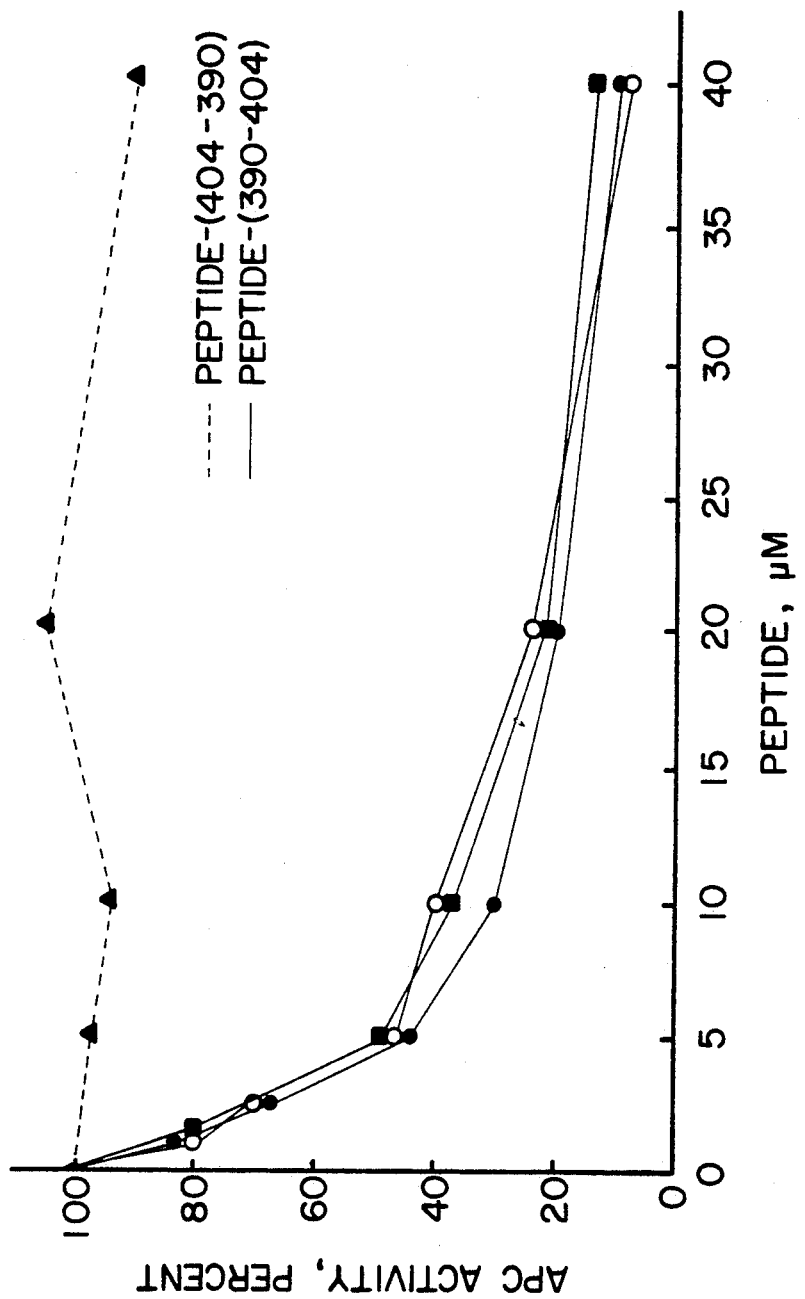
FIG. 3 illustrates the inhibition of APC anticoagulant activity by peptide-(390-404) in APTT and Xa-1-stage coagulation assays. The assays were performed as described in Examples 5a1) and 5a2). Solid lines with solid circles represent inhibition of anticoagulant activity of 2.5 nM APC by peptide-(390-404) in an APTT assay in normal human plasma, solid lines with open circles represent inhibition of anticoagulant activity of 5.0 nM APC by peptide-(390-404) in an APTT assay in protein S depleted plasma, solid lines with solid squares represent inhibition of anticoagulant activity of 30.0 nM APC by peptide-(390-404) in a Xa-1-stage assay in factor VIII deficient plasma and dashed lines with solid triangles represent APC activity (2.5 nM APC in APTT) in the presence of peptide-(404-390) as a control. All data represent mean values of APC anticoagulant activity from two different experiments performed on two different days as derived from the corresponding APC standard curves All clotting times were done in duplicate

The results of the inhibition of APC anticoagulant activity by peptide-(390-404) compared to peptide-(404-390) in APTT and Xa-1-stage coagulations assays are shown in FIG. 3. All data represent mean values of APC anticoagulant activity from two different experiments performed on two different days as derived from the corresponding APC standard curves. The same dose-response curves of inhibition of APC activity by peptide-(390-404) were obtained in either APTT or Xa-1-stage coagulation assays as shown in FIG. 3. In both assays, peptide-(390-404) had a half-maximal inhibition (IC₅₀) with 5 μM peptide and an IC₉₀ with 40 μM peptide. Thus, peptide-(390-404) is specific for APC since it dose-dependently and reproducably inhibited APC activity in two different coagulation assays in the presence of different plasma preparations.

In addition, the same dose-response curve of APC inhibition by peptide-(390-404) was obtained when the APTT assay was performed in the presence of PSDP instead of NHP (FIG. 3). This suggests that the inhibitory effect of peptide-(390-404) is not dependent on the presence of the APC co-factor, Protein S, and that the interaction between APC and PS is not disturbed by the peptide.

The specificity of the peptide-(390-404) for inhibiting APC anticoagulant activity was further supported by the fact that peptide-(404-390) had no APC inhibitory activity when measured in an APTT assay as shown in FIG. 3. In addition, in APTT assays performed in the absence of the anticoagulant APC at the ranges of concentrations evaluated for each of the above-identified peptides, no significant inhibition of either APTT or Xa-1-stage coagulation assays was observed.

3) Amidolytic Activity of APC Assay

The effects of PC-derived inhibitory synthetic peptides on the amidolytic activity of APC were evaluated to determine if the peptides inhibited APC anticoagulant activity by blocking a region in or close to the active site of the enzyme involved in cleavage of a small substrate such as S-2366 (Kabi-Vitrum) or involved in the site of interaction with the recombinant mutant (Arg³⁵⁸)α₁-antitrypsin (α₁-AT) (Transgene, Strasbourg, France), the latter of which is described in Example 5a4) below. The assay was performed as described by Marlar et al., supra; and Suzuki et al., supra.

The amidolytic activity of APC toward the peptide substrate S-2366 was measured in the presence of various PC synthetic peptides prepared in Example 1. For the assay, 100 μl of 15 nM APC, prepared in Example 2c2), was admixed with separate aliquots of peptide-(390-404) ranging in concentration from 0.0 to 750 μM prepared in TBS-BSA at pH 7.4 containing 0.02% NaN₃ and 2 mM CaCl₂ to form APC-peptide admixtures, respectively. After maintenance of the admixtures for 30 minutes at 37° C., 50 μl of 2.4 mM S-2366 in the same buffer was admixed to initiate the amidolytic reaction. The hydrolysis of the substrate was monitored by the change in absorbance at 405 nm at 37° C. over time using an EL312 Microplate Bio-Kinetics Reader (BIO-TEK Instruments, Inc. Vt.).

In contrast to the inhibitory effects of synthetic peptides on APC anticoagulant activity, peptides-(390-404), -(396-410), -(384-398), -(311-325) and -(317-331) at all concentrations up to 500 μM did not significantly alter APC amidolytic activity towards the chromogenic substrate, S-2366 as shown in Table 5 below. These results indicate that these peptides do not exert inhibitory effects of APC anticoagulant activity by blocking a region in or close to the active site of the enzyme involved in cleavage of a small substrate.

TABLE 5

| APC Amidolytic Activity in the Presence of Peptides and Anti-(390-404) Antibody Towards S-2366 | | | |
|---|---|---|---|
| APC | | Peptide/Antibody | A₄₀₅/5 min |
| APC | | — | 0.374 |
| APC | + | 500 μM | -(390-404) 0.371 |
| APC | + | 500 μM | -(396-410) 0.364 |
| APC | + | 500 μM | -(384-398) 0.378 |
| APC | + | 250 μM | -(311-325) 0.342 |
| APC | + | 500 μM | -(317-331) 0.383 |
| APC | + | 330 nM | Anti-(390-404) 0.386 |
| — | | — | 0.001 |

4) Inhibition of APC by Recombinant Mutant α₁-Antitrypsin Assay

Since the number of amino acid residues involved in protease-protease inhibitor complexes is likely to be higher than the number of residues of APC involved in the cleavage of a small chromogenic substrate such as S-2366, the effect of peptide-(390-404) and peptide-(317-331) on the time course of inhibition of APC by a larger pseudosubstrate, recombinant mutant (Arg³⁵⁸)-α₁-antitrypsin (α₁-AT) was evaluated. The substitution of Met³⁵⁸ by Arg in the reactive center of recombinant α₁-AT has been shown to result in an increase of over 4400-fold in the association rate for APC. Heeb et al., *J. Biol. Chem.* 265:2365–2369 (1990).

Kinetic studies of inhibition of APC were performed with the higher affinity mutant α₁-AT pseudo-substrate. For the assay, 60 μl of 36 nM APC and/or 60 μl of 200 nM recombinant (Arg³⁵⁸)-α₁-AT prepared in TBS-BSA at pH 7.4 containing 0.02% NaN₃ and 2 mM CaCl₂ were separately admixed with 200 μM peptide-(390-404) or 1 mM peptide-(317-331) and maintained for 30 minutes at 37° C. to form APC-peptide and/or $\alpha_1$-AT-peptide admixtures, respectively. Thereafter, the peptide-treated APC and $\alpha_1$-AT admixtures were combined to form a reaction admixture. At selected time points, 8 μl aliquots from the reaction admixture were removed and admixed with 300 μl 0.8 mM S-2366 in TBS-BSA at pH 8.0 containing 0.02% NaN$_3$ to initiate the hydrolysis of S-2366 by APC. The change in absorbance was measured over time as described in the amidolytic assay. Controls without the inhibitor $\alpha_1$-AT in the absence or presence of peptides were included in the assay.

Figure 4:
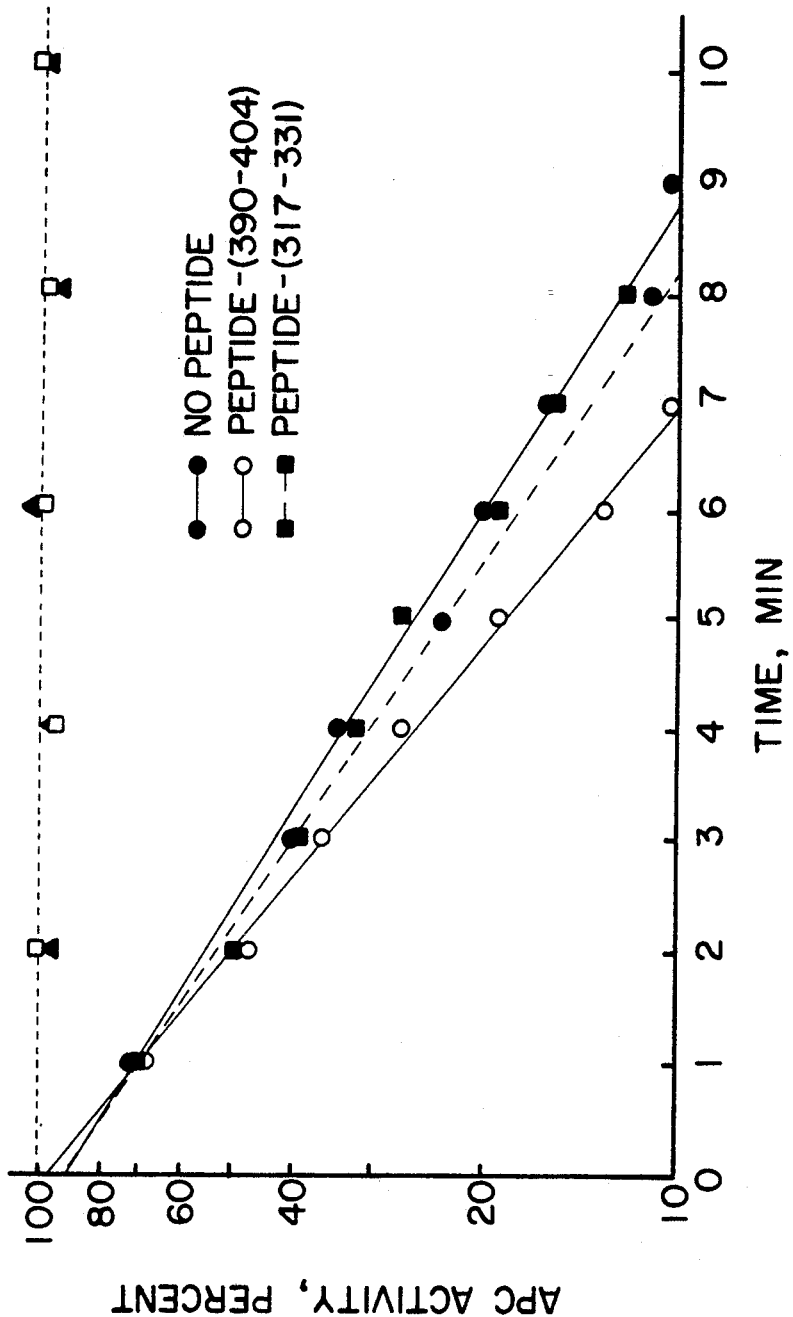
FIG. 4 illustrates the inhibition of APC by recombinant [Arg$^{358}$]$\alpha_1$-antitrypsin (AT) in the absence or presence of peptide-(390-404) or peptide-(317-331) assessed on semilog plots. The assay was performed as described in Example 5a4). Solid lines with solid circles denote inhibition of APC by [Arg$^{358}$]$\alpha_1$-AT in the absence of peptides. Solid lines with open circles denote inhibition of APC by [Arg$^{358}$]$\alpha_1$-AT in the presence of 100 $\mu$M peptide-(390-404) and dashed lines with solid squares denote inhibition of APC by [Arg$^{358}$]$\alpha_1$-AT in the presence of 500 $\mu$M peptide-(317-331). APC activity in the absence of $\alpha_1$-AT but in the presence of 100$\mu$M peptide-(390-404) is indicated by closed triangles and in the presence of 500 $\mu$M peptide-(317-331) is indicated by open squares. The APC concentration was 18 nM and the concentration of $\alpha_1$-AT 100 nM. Linear regression analysis (APC activity in percent was logarithmically transformed) was performed from each set of data (with the exception of the controls) and the correlation ranged from $-0.995$ to $-0.998$.

APC activity in the controls performed above was constant with a deviation of 5% over the course of the experiment. Peptide-(390-404), in addition to peptide-(317-331), at final concentrations of 100 μM and 500 μM, respectively, did not have any significant effect on the time course of inhibition of APC by recombinant (Arg$^{358}$)$\alpha_1$-AT as shown in FIG. 4. In addition, APC activity in the presence of either peptide but in the absence of $\alpha_1$-AT was not inhibited over the assayed time course of 10 minutes. The calculated half-life of 2 minutes for APC under the assay conditions with final concentrations of 18 nM APC and 100 nM $\alpha_1$-AT agreed with the recently reported half-life of APC. Heeb et al., supra. These results, which are consistent with the amidolytic assay results described above, provide additional support that the APC inhibitory peptides do not act by blocking a region in or close to the active site of the enzyme or other important sites involved in interactions with the recombinant mutant $\alpha_1$-AT.

5) Inactivation Assay of Factor Va by APC

Since the peptide-(390-404) was shown to be a potent inhibitor of APC anticoagulant activity in coagulation assays described in Examples 5a1) and 5a2), the peptide was also evaluated for its ability to inhibit the APC-catalyzed inactivation of Factor Va in the presence of phospholipid vesicles in a purified system using APC. The assay consisted of two parts wherein the APC catalyzed inactivation of Factor Va in the absence or presence of peptides was tested in the first part followed by the indirect determination of remaining Factor Va activity in a prothrombinase assay in the second part.

Inactivation of Factor Va by APC

The APC catalyzed inactivation of Factor Va assays were performed in 96-well flat bottom ELISA plates (Stockwell Scientific, Walnut, Calif.). The reactions were performed either in the presence or absence of phospholipid vesicles to determine if peptide-(390-404) inhibited APC anticoagulant activity by inhibiting the binding of APC or its substrate to phospholipids or if it was independent of phospholipid surfaces. This determination was relevant in light of reports that the assembly of APC with its substrates Va and VIIIa on the phospholipid surface appeared to be mediated mainly by the Gla-domain of APC in the presence of calcium which was crucial for exerting significant anticoagulant activity. [Sugo et al., *J. Biol. Chem.*, 260:10453-10457 (1985); Krishnaswamy et al., *J. Biol. Chem.*, 261:9684-9693 (1986); Solymoss et al., *J. Biol. Chem.*, 263:14884-14890 (1988)].

For the preparation of phospholipid residues for use in the assay bovine brain phosphatidylserine in chloroform (CCl$_4$)/methanol (CH$_3$OH) and soybean phosphatidylcholine (Type III-S, CCl$_4$ solution) were purchased from Sigma and were reported to be at least 98% homogeneous (supplier's estimates). To prepare vesicles, phosphatidylserine was admixed with phosphatidylcholine (20% phosphatidylserine/80% phosphatidylcholine; M/M) and the organic solvent evaporated under a stream of nitrogen. The resultant phospholipid admixture was resuspended in 0.05M TBS-Az at pH 7.4 as a 1.25 mM solution by vortexing. Single bilayer vesicles were obtained during sonication by direct probe (Heat-systems-Ultrasonics, Inc., W-220F Sonicator) for 6×30 second bursts at 30W in 2 minute intervals at 4° C.

The reaction buffer consisted of 0.05M Tris-HCl, at pH 7.4 containing 0.1M NaCl, 0.02% NaN$_3$, 0.5% BSA and 2.5 mM CaCl$_2$. Reactions were performed in reaction buffer in the absence or presence of 50 μM phospholipid vesicles (20% phosphatidylserine/80% phosphatidylcholine; M/M) either at 22° C. (in the presence of phospholipids) or at 37° C. (in the absence of phospholipids). In the presence of phospholipids, the final APC concentration was ≦0.25 nM with 10.0 nM Va and in the absence of phospholipids the final APC concentration was 5.0 nM APC with 40.0 nM Va. Before admixing APC to the solution containing Factor Va, a 5 μl aliquot admixed to 95 μl of 1.5 μg/ml (at APC up to 0.25 nM) or 20 μg/ml (at 5.0 nM APC) immunoaffinity-purified monoclonal antibody C3 in TBS-BSA. The monoclonal antibody C3 specifically recognizes the light-chain of PC as well as APC was prepared as in Example 2. Factor Va (a gift from Drs. Tans and Rosing, Univ. of Limburg, the Netherlands) was first admixed with or without peptide-(390-404) and maintained for 20 minutes either at 22 C or at 37° C. prior to admixture with APC. After admixture of an equal volume of APC with the pretreated-Va-containing solution, 10 μl aliquots were removed at appropriate short time intervals (30 seconds up to 2.5 minutes) and the reaction was then quenched by the addition to 90 μl of immunoaffinity-purified C3 antibody. Controls confirmed that the APC inactivation of Va was completely quenched by this procedure, that Factor Va remained stable over the course of the experiment and that neither the C3 antibody nor the peptide-(390-404) had any effect on the subsequent measurement of residual Factor Va activity in the prothrombinase by itself.

After sample collection, an aliquot of this solution was assayed for Va activity as described below. Since in the presence of phospholipids the APC-catalyzed inactivation obeys second order kinetics, the first-order rate-constants ($k_1$-values) were calculated from the slopes of the plots of the logarithm of residual Va activity over time before 40% of Va was consumed. Tans et al., *Blood*, in press. These initial slopes were found to be linear. In the range from 0.0 up to 0.25 nM APC with 10.0 nM Va, the observed $k_1$-value was linearly dependent on the APC concentration. The measured APC activity in percent, in the presence of peptide-(390-404), was determined by referring the observed $k_1$-values to the APC standard curve of $k_1$-values at known APC concentrations. The inactivation of Factor Va by APC in the absence of phospholipids was linear over time until 40-50% of Factor Va had been consumed.

Factor Va-Prothrombinase Assay

Factor Va was determined via its cofactor activity in the activation of prothrombin by Factor Xa. Amounts of Factor Xa (Enzyme Research Lab.), phospholipid vesicles and prothrombin (purified as described by Stenflo, *J. Biol. Chem.* 25:355-363, (1976) from a barium citrate plasma precipitate purified by DEAE-sephadex chromatography) present in the assay were such that the rate of prothrombin activation was linearly dependent on factor Va and constant over the time course of the experiment. The molar concentration of Factor Xa was determined by active site titration as described by Chase et al., *Biochem. Biophys. Res. Commun.*, 29:508-514 (1967). The molecular weights and extinction coefficients ($E_{280\ nm}$/mg/ml) used in the calculation of protein concentrations were as follows: prothrombin, 72,000 and 1.44; APC, 62,000 and 1.45; and Factor Xa, 65,300 and 1.16.

In a typical experiment, Factor Va was assayed as follows. An aliquot of the solution containing Va was admixed to a solution containing prothrombin, phospholipids and calcium in individual wells of a 96-well microtiter plate. Prothrombin activation was initiated with the mixture of Factor Xa to the Va-containing wells to form a reaction admixture. Final concentrations of reagents in the reaction mixture were the following: 1.2 $\mu$M prothrombin, 1 nM Xa, 0-0.4 nM Va, 50 $\mu$M phospholipid-vesicles (phosphatidylserine 20%/phosphatidylcholine 80%; M/M), in 0.05M Tris-HCl at pH 7.4 containing 0.1M NaCl, 0.5% BSA and 2.0 mM $CaCl_2$. The reaction was maintained at 22° C. At one minute intervals from initiation of the reaction, 20 $\mu$l aliquots of the reaction admixture were withdrawn and admixed to wells of an ELISA plate containing 80 $\mu$l TBS-BSA and 10 mM EDTA at pH 8.0 resulting in the quenching of the prothrombinase reaction. After sample collection, 50 $\mu$l of 2.0 mM S-2238 in TBS-BSA and 10 mM EDTA at pH 8.0 was admixed to the quenched reaction admixture and the amidolytic activity of the generated thrombin towards the chromogenic substrate S-2238 was then monitored by measuring the absorbance at 405 nm over time using EL312 Kinetics Reader and the Kineticalc Software Program (Biotek). The amount of thrombin formed over time was linearly dependent on Factor Va (up to 0.4 nM Va). From a standard curve with known amounts of Factor Va the amount of Factor Va present in the reaction mixture was calculated.

Figure 5:
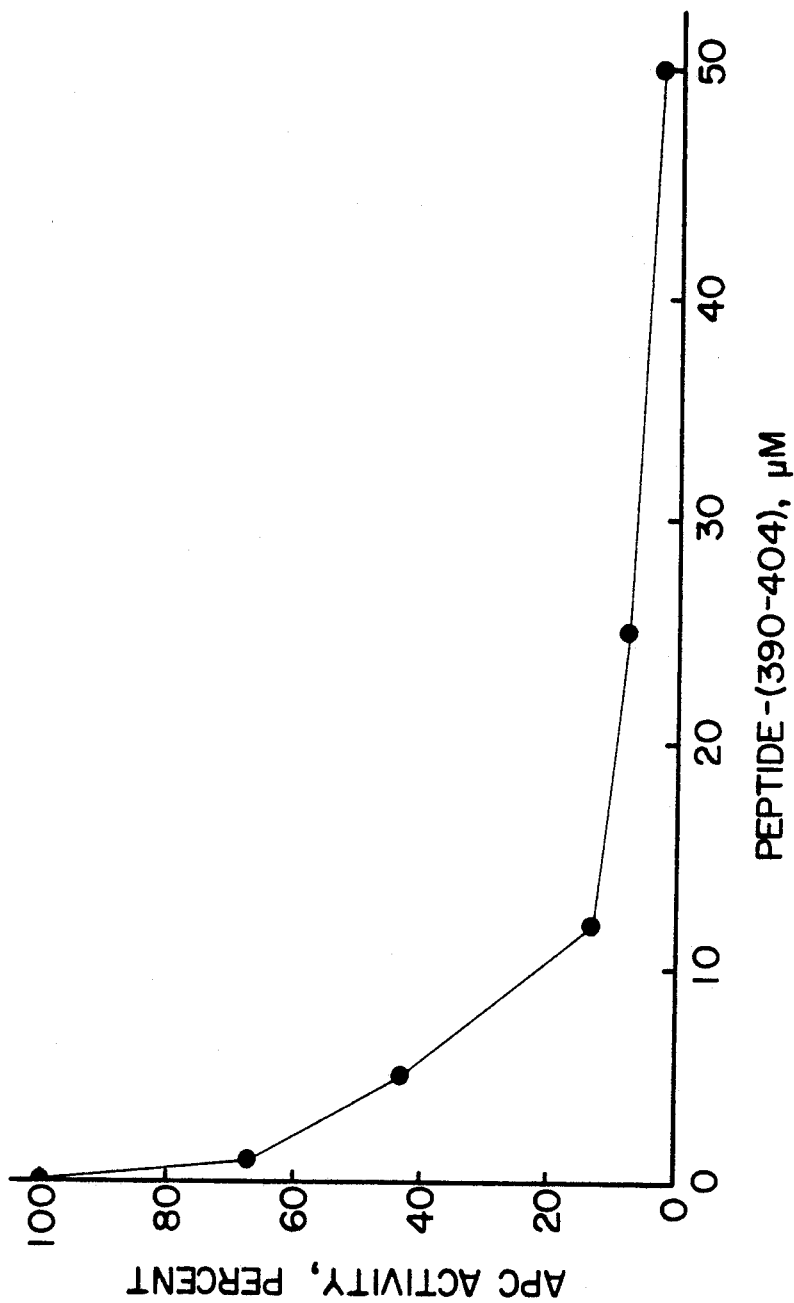
FIG. 5 illustrates the APC-catalyzed inactivation of Factor Va in the presence of peptide-(390-404) and phospholipids. The assay was carried out in TBS-BSA and 2.5 mM CaCl$_2$ at pH 7.4 as described in Example 5a5) using 0.25 nM APC, 10.0 nM Va, 50 $\mu$M phospholipid vesicles and 0 to 50 $\mu$M peptide-(390-404), that had been preincubated for 20 minutes at 22° C. with Factor Va. Factor Va inactivation by APC was indirectly determined using the cofactor activity of Factor Va in a prothrombinase assay as described in Example 5a5). Residual APC activity in the presence of the peptide was calculated from a standard curve.

As shown in FIG. 5, peptide-(390-404) dose-dependently inhibited the APC-catalyzed inactivation of Factor Va with half-maximal inhibition at 4 $\mu$M. Moreover, peptide-(390-404) inhibited the APC-catalyzed inactivation of Factor Va in the absence of phospholipids. Using 5 nM APC and 40 nM Va, the rate of Factor Va inactivation (% $V_i$/min) was measured to be 3.1% $V_i$/min in the absence of peptide and 0.2% $V_i$/min in the presence of 50 $\mu$M peptide-(390-404) corresponding to 94% inhibition of APC activity in this assay.

Thus, the observation that peptide-(390-404) inhibited APC-catalyzed inactivation of purified Factor Va in the presence as well as in the absence of phospholipids with a similar dose response as in the coagulation system excludes the possibility that peptide-(390-404) inhibits binding of APC or its substrate Factor Va to phospholipids.

b. Inhibition of APC by Anti-Peptide-(390-404) Antibody

The immunoaffinity-purified polyclonal anti-peptide-(390-404) antibody prepared in Examples 2 and 3 was screened for its ability to inhibit APC anticoagulant activity in four different assays as described above in which synthetic PC-derived peptides were evaluated. The assays were used to verify the implications from the data obtained by peptide-(390-404) that this region in APC is essential for the protein's anticoagulant activity and for the recognition of the macromolecular substrates, activated Factors V (Va) and VIII (VIIIa).

1) Activated Partial Thromboplastin Time (APTT) Coagulation Assay

The effect of the immunoaffinity-purified polyclonal anti-peptide-(390-404) antibody, hereinafter referred to as anti-(390-404), on APC anticoagulant activity was determined using the APTT assay as described in Example 5a1).

For the APTT assay, APC was prepared as described in Example 2c2). The specific anticoagulant activity of APC was determined to be 250 Units/mg. The concentration of the APC used in the assay was initially optimized with respect to the sensitivity of the assay towards APC-induced prolongation of clotting time compared to clotting time without APC.

Once the optimal concentration of APC was determined, anti-(390-404) was separately admixed ranging in concentration from 0.0 to 240 nM with APC in 200 $\mu$l of TBS-BSA and 30 mM $CaCl_2$ at pH 7.4 to form an anti-(390-404)-APC immunoreaction admixture pre-maintenance solution. For APTT assays in the presence of NHP, APC was used at a concentration of 5 nM. For APTT assays in the presence of PSDP, APC was used at a concentration of 10 nM. The resulting admixtures were maintained for 30 minutes at 37° C. to allow formation of an immunoreaction product. Separate aliquots of APC maintained under the same conditions in the absence of anti-(390-404) antibody but in the presence of non-immune rabbit IgG served as controls for the inhibitory effect of anti-peptide antibodies on APC anticoagulant activity. Concurrently, 100 $\mu$l of NHP and 100 $\mu$l APTT-reagent Thrombosil (Ortho Diagnostics) were admixed together and maintained for 200 seconds at 37° C. to form a plasma-reagent admixture. In some experiments, PSDP was used in the place of NHP to determine the effect of Protein S on the assay system. Coagulation was then initiated by the admixture of 200 $\mu$l of the pre-maintenance solution containing TBS-BSA and 30 mM $CaCl_2$ with or without the APC which was either exposed to anti-(390-404) antibody or not. The time for clot formation was measured as described in Example 5a1). The anti-(390-404) antibody effect was determined in duplicate. The results of the APTT assays are discussed below with the results from similar analyses using the Xa-1-stage coagulation assay.

2) Xa-1-Stage Coagulation Assay

For testing the inhibition of the anti-(390-404) antibody on APC activity described above, Xa-1-stage coagulation assays were also performed as described in Example 5a2). Anti-(390-404) antibody was prepared as described above and separately admixed with 60 nM APC in 200 $\mu$l of 0.31 nM human Factor Xa prepared as described in Examples 5a2) and 5a5) in TBS-BSA and 30 mM $CaCl_2$ at pH 7.4 to form an anti-(390-404) antibody-APC pre-maintained immunoreaction admixture. The resulting admixtures were maintained for 30 minutes at 37° C. to allow formation of an immunoreaction product. Separate aliquots of APC maintained under the same conditions in the absence of anti-(390-404) antibody but in the presence of non-immune rabbit IgG served as controls for the inhibitory effect of anti-(390-404) antibody on APC anticoagulant activity. Concurrently, 100 μl of NHP and 100 μl of 200 μg/ml of rabbit brain cephalin (Sigma) were admixed and maintained for 200 seconds at 37° C. to form a plasma-phospholipid admixture. In some experiments, Factor VIII deficient plasma (George King Bio-Medical, Inc.) was used in the place of NHP to determine the effect of Factor VIII on the assay system. Coagulation was then initiated by the admixture of 200 μl of the pre-maintained mixture containing 0.31 nM human Factor Xa prepared as described in Examples 5a2) and 5a5) in TBS-BSA containing 30 mM $CaCl_2$ with or without 60 nM of APC which was either exposed to anti-(390-404) antibody or not.

Figure 6:
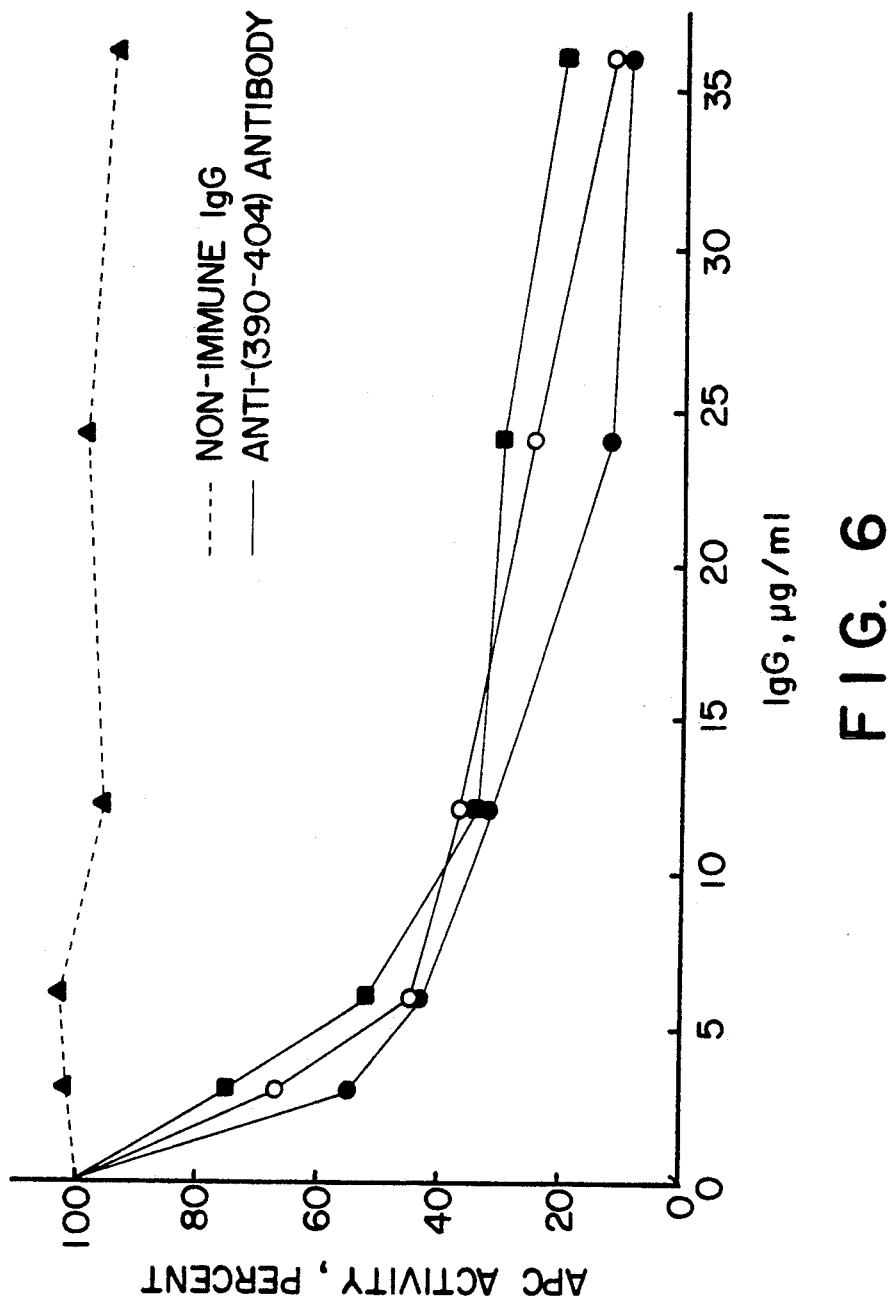
FIG. 6 illustrates the inhibition of APC anticoagulant activity by immunoaffinity purified anti-(390-404) antibody in APTT and Xa-1-stage coagulation assays. The assays were performed as described in Example 5b1) and 5b2). Solid lines with solid circles represent inhibition of the anticoagulant activity of 2.5 nM APC by anti-(390-404) antibody in an APTT assay using normal human plasma, solid lines with open circles represent inhibition of anticoagulant activity of 5.0 nM APC by anti-(390-404) antibody in an APTT assay in protein S depleted plasma and solid lines with solid squares represent inhibition of anticoagulant activity of 30.0 nM APC by anti-(390-404) antibody in a Xa-1-stage assay using factor VIII deficient plasma. Dashed lines with solid triangles indicate anticoagulant activity of 2.5 nM APC in APTT in normal human plasma in the presence of non-immune rabbit IgG as negative control.

The time for clot formation was measured as described in Example 5a2). The effects of anti-(390-404) antibody were determined in duplicate. The results of the inhibition of APC anticoagulant activity by anti-(390-404) as measured in APTT and Xa-1-stage coagulation assays are shown in FIG. 6. All data represent mean values of APC anticoagulant activity from two different experiments performed on two different days as derived from the corresponding APC standard curves. The dose-response of anti-(390-404) antibody inhibition of APC anticoagulant activity in NHP was similar to that observed in PSDP and in Factor VIII deficient plasma with a 50% inhibition occurring at 20 to 40 nM of anti-(390-404) antibody. The same dose-response curve was observed in a Xa-1-stage assay using PSDP (data not shown). Non-immune polyclonal rabbit IgG, that failed to recognize PC or APC as determined by ELISA, did not inhibit APC anticoagulant activity. These results are similar to those obtained with coagulation assays performed in the presence of inhibitory synthetic peptides (refer to Examples 5a1) and 5a2).

Thus, the anti-(390-404) antibody is highly specific for the peptide against which it was raised as described in Example 2c but is also highly specific for APC and PC as well as indicated by the inhibitory effects of APC anticoagulant activity and indicated by the fact that the anti-(390-404) antibody had no effect on APTT and Xa-1-stage coagulation assays in the absence of APC. The fact that the dose-response curve for inhibiting APC anticoagulant activity in NHP was almost identical to that observed in PSDP indicates that the antibody does not interfere with the interaction of APC with its cofactor protein S. Thus, residues 390-404 of APC are probably not involved with interactions with protein S.

3) Amidolytic Activity of APC Assay

The effect of anti-(390-404) antibody on the amidolytic activity of APC was evaluated to determine if the antibody inhibited APC anticoagulant activity by blocking a region in or close to the active site of the enzyme involved in cleavage of a small substrate such as S-2366 (Kabi-Vitrum) or involved in the site of interaction with the recombinant mutant $(Arg^{358})\alpha_1$-AT, the latter of which is described in Example 5b4) below.

The amidolytic activity of APC toward the peptide substrate S-2366 was measured in the presence of anti-(390-404) antibody. For the assay, 100 μl of 15 nM APC, prepared in Example 2c2), were admixed with separate aliquots of anti-(390-404) antibody ranging in concentration from 0.0 to 500 nM prepared in TBS-BSA at pH 7.4 containing 0.02% $NaN_3$ and 2 mM $CaCl_2$ to form APC-anti-(390-404) antibody immunoreaction admixtures, respectively. After maintenance of the admixtures for 30 minutes at 37° C. to allow formation of immunoreaction products, 50 μl of 2.4 mM S-2366 in the same buffer was admixed to initiate the amidolytic reaction. The hydrolysis of the substrate was monitored by the change in absorbance at 405 nm over time using an EL312 Microplate Bio-Kinetics Reader (BIO-TEK Instruments, Inc. Vt.).

In contrast to the inhibitory effect of anti-(390-404) antibody on APC anticoagulant activity, 0.0 to 500 nM anti-(390-404) antibody admixed with 15 nM APC for 30 minutes at 37° C. had no influence on APC amidolytic activity using the chromogenic substrate S-2366 as shown in Table 5. These results indicate that anti-(390-404) antibody, like peptides-(390-404) and -(317-331), does not exert inhibitory effects of APC anticoagulant activity by blocking a region in or close to the active site of the enzyme involved in cleavage of a small substrate.

4) Inhibition of APC by Recombinant Mutant $\alpha_1$-Anti-Trypsin Assay

Since the number of amino acid residues involved in protease-protease inhibitor complexes is likely to be higher than the number of residues of APC involved in the cleavage of a small chromogenic substrate such as S-2366, the effect of anti-(390-404) antibody on the time course of inhibition of APC by a larger pseudo-substrate, such as recombinant mutant $(Arg^{358})$-$\alpha_1$-AT was evaluated. Kinetic studies of inhibition of APC were performed with the high affinity mutant $\alpha_1$-AT pseudo-substrate. For the assay, 60 μl of 36 nM APC was admixed with 580 nM anti-(390-404) antibody to form an APC-antibody immunoreaction admixture which was maintained for 30 minutes at 37° C. to allow formation of immunoreaction product in TBS-BSA at pH 8.0 containing 0.02% $NaN_3$ and 2 mM $CaCl_2$. After the maintenance period, the APC-antibody immunoreaction product was then admixed with 60 μl of 200 nM recombinant $(Arg^{358})$-$\alpha_1$-AT prepared as described in Example 5a4). At selected time points, 8 μl aliquots from the reaction admixture were removed and admixed with 300 μl 0.8 mM S-2366 in TBS-BSA at pH 7.4 containing 0.02% $NaN_3$ to initiate the hydrolysis of S-2366 by APC. The change in absorbance was measured over time as described in the amidolytic assay. Controls without the inhibitor $\alpha_1$-AT in the absence or presence of antibody were included in the assay.

Figure 7:
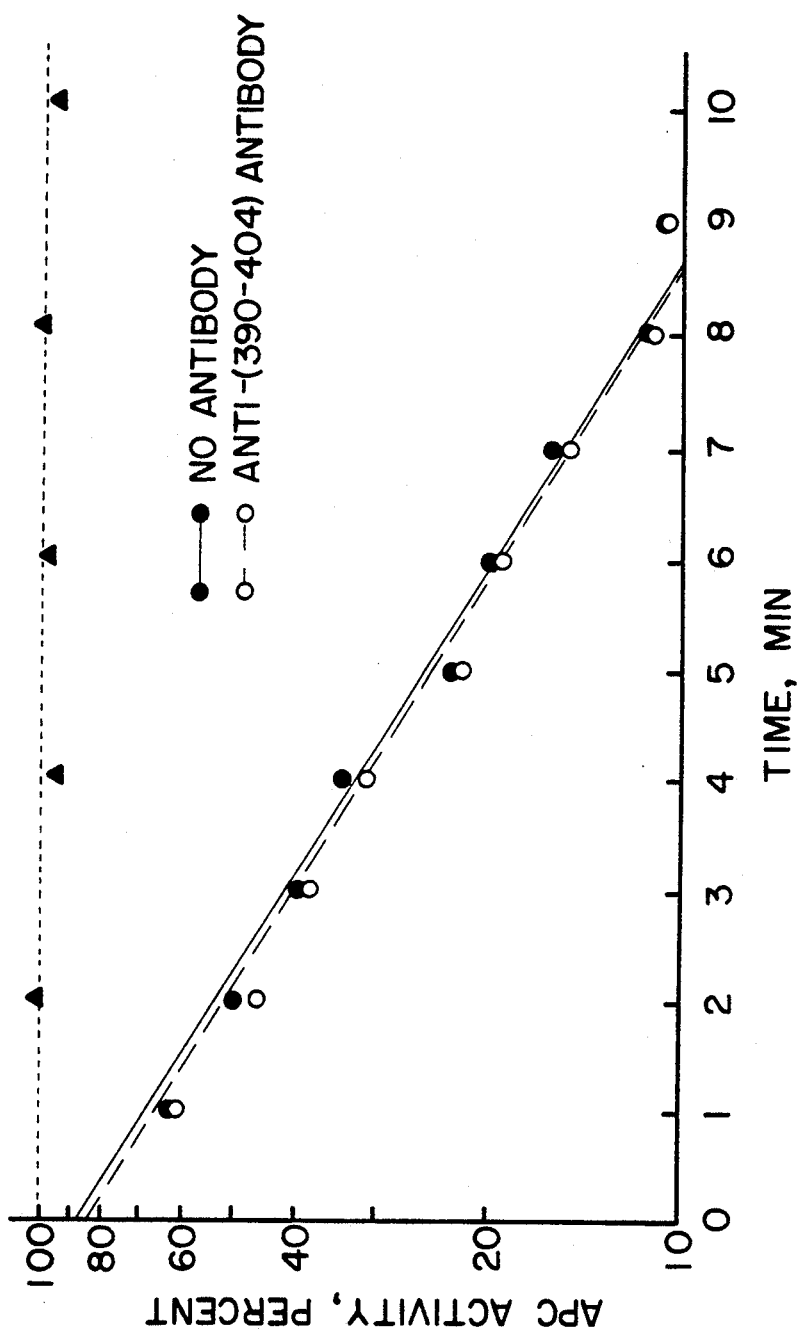
FIG. 7 illustrates the inhibition of APC by recombinant [Arg$^{358}$]$\alpha_1$-AT in the absence or presence of immunoaffinity purified anti-(390-404) antibody assessed on semilog plots. The assays were performed as described in Example 5b4). Solid lines with solid circles denote inhibition of 18 nM APC by 100 nM $\alpha_1$-AT in the absence of anti-(390-404) antibody and dashed lines with open circles denote inhibition of 18 nM APC by 100 nM $\alpha_1$-AT in the presence of 290 nM anti-(390-404). The antibody had been pre-maintained with APC for 30 minutes at 37° C. before admixing with $\alpha_1$-AT. Dashed lines with solid triangles represent mean values of APC activity in the absence of $\alpha_1$-AT but in the presence of 290 nM anti-(390-404) antibody which served as control. Linear regression analysis (APC activity in percent was logarithmically transformed) was performed for both sets of data (except for the controls) and the correlation was $-0.993$ and $-0.992$, respectively.

APC activity in the controls performed above was constant with a deviation of 5% over the course of the experiment. Anti-(390-404) antibody at a final concentration of 290 nM did not have any significant effect on the time course of inhibition of 18 nM APC by 100 nM recombinant $(Arg^{358})\alpha_1$-AT as shown in FIG. 7. In addition, APC activity in the presence of either anti-(390-404) antibody but in the absence of $\alpha_1$-AT was not inhibited over the assayed time course of 10 minutes. These results which are consistent with the results obtained with synthetic peptides and with the amidolytic assay results described above provide additional support that the antibody directed against the peptide corresponding to the 390-404 amino acid residue sequence on APC does not act by blocking a region in or close to the active site of the enzyme or other important regions involved in interactions with the recombinant mutant $\alpha_1$-AT.

6. Comparison of the Inhibition of APC Anticoagulant Activity by Peptide-(390-404) and Anti-(390-404) Antibody The peptide-(390-404) and the specific anti-peptide antibody, anti-(390-404), described above exhibited qualitatively similar results as far as their influence on APC activity is concerned. They both potently inhibited APC anticoagulant activity in an APTT assay as well as in a Xa-1-stage coagulation assay in different plasma sources (NHP, PSDP and VIII deficient plasma), but did not inhibit the cleavage of S-2366 by APC or the interaction of APC with a serpin-like recombinant $\alpha_1$-AT mutant.

The additional observation that peptide-(390-404) inhibited APC-catalyzed inactivation of purified Factor Va in the presence as well as in the absence of phospholipids with a similar dose response as in the coagulation assay system excludes the possibility that peptide-(390-404) inhibits binding of APC or its substrate Factor Va to phospholipids.

Therefore, the region of residue 390-404 represents an exosite in APC essential for its anticoagulant activity and for the recognition of its macromolecular substrates Factor Va and VIIIa but this exosite is not involved in substrate recognition near the active site or APC interaction with protein S. This result is supported by the fact that the location of this region in the three-dimensional model of chymotrypsinogen based on x-ray crystallographic data represents a highly conserved exosite that is distant from the hydrophobic substrate binding pocket of the catalytic domain. The region of residues 225-239 in chymotrypsinogen (homologous to 390-404 in PC) is partially buried (residue 225-229 forms a $\beta$-strand with residue 214-219) whereas residue 230-239 form an $\alpha$-helix that is surface exposed and could potentially mediate the binding of the enzyme to its macromolecular substrates Va and VIIIa but is unlikely to be involved in APC interaction with smaller substrates. This inference is reasonable, because of the sequence homology observed for the heavy chain of APC and other serine proteases and because this class of enzymes seems to have a common three dimensional structure allowing, within a reasonable range an interpretation of structure-function relationships of APC using models based on the conformation of evolutionary related enzymes.

The foregoing specification, including the specific embodiments and examples, is intended to be illustrative of the present invention and is not to be taken as limiting. Numerous other variations and modifications can be effected without departing from the true spirit and scope of the present invention.

---

100
SEQUENCE LISTING

SEQ ID NO 1:
158    DTEDQEDQVDPRLIDGKMTRRGDSPWQVVLLDSKKKLACGAVL
IHPSWVLTAAHCMDESKKLLVRLGEYDLRRWEKWELDLDIKEVFVHPNYS
KSTTDNDIALLHLAQPATLSQTIVPICLPDSGLAERELNQAGQETLVTGW
GYHSSREKEAKRNRTFVLNFIKIPVVPHNECSEVMSNMVSENMLCAGILG
DRQDACEGDSGGPMVASFHGTWFLVGLVSWGEGCGLLHNYGVYTKVSRYL
DWIHGHIRDKEAPQKSWAP    419

---

What is claimed is:

1. A protein C polypeptide comprising no more than 100 amino acid residues and including an amino acid residue sequence represented by the formula: —YG-VYTXVSRYLDWIH—, said sequence shown in SEQ ID NO 1 from residue 390 to residue 404, wherein X is either K or A, and wherein said polypeptide inhibits activated protein C without inhibiting activated protein C amidolytic activity and without effecting inhibition of activated protein C by $\alpha_1$-antitrypsin.

2. The polypeptide of claim 1 wherein X is K and said polypeptide comprises an amino acid residue sequence corresponding to the amino acid residue sequence of protein C shown in SEQ ID NO 1.

3. The polypeptide of claim 1 wherein said polypeptide has an amino acid residue sequence represented by a formula selected from the group consisting of:

YGVYTKVSRYLDWIH,
YGVYTKVSRYLDWIHGHIRDK,
CGLLHNYGVYTKVSRYLDWIH,
CGLLHNYGVYTKVSRYLDWIHGHIRDK,
SGLLHNYGVYTKVSRYLDWIHGHIRDK,
SGLLHNYGVYTKVSRYLDWIH, and
YGVYTAVSRYLDWIH, said sequences shown in SEQ ID NO 1 from residue 390 to residue 404, from residue 390 to residue 410, from residue 384 to residue 404, from residue 384 to residue 410, shown in SEQ ID NO 3 from residue 384 to residue 410, shown in SEQ ID NO 3 from residue 384 to residue 404 , and shown in SEQ ID NO 4 from residue 390 to residue 404, respectively.

4. A protein C polypeptide comprising no more than 100 amino acid residues and including an amino acid residue sequence represented by the formula: —YGVYTKVSR—, said sequence shown in SEQ ID NO 1 from residue 390 to residue 398, and wherein said polypeptide inhibits activated protein C without inhibiting activated protein C amidolytic activity and without effecting inhibition of activated protein C by $\alpha_1$-antitrypsin.

5. The polypeptide of claim 4 wherein said polypeptide has an amino acid residue sequence represented by a formula selected from the group consisting of:

YGVYTKVSR,
CGLLHNYGVYTKVSR, and
SGLLHNYGVYTKVSR, said sequences shown in SEQ ID NO 1 from residue 390 to residue 398, from residue 384 to residue 398, and shown in SEQ ID NO 3 from residue 384 to residue 398, respectively.

6. A protein C polypeptide comprising no more than 100 amino acid residues and including an amino acid residue sequence represented by the formula: —VSRYLDWIH—, said sequence shown in SEQ ID NO 1 from residue 396 to residue 404, and wherein said polypeptide inhibits activated protein C without inhibiting activated protein C amidolytic activity and without effecting inhibition of activated protein C by $\alpha_1$-antitrypsin.

7. The polypeptide of claim 6 wherein said polypeptide has an amino acid residue sequence represented by a formula selected from the group consisting of:

VSRYLDWIH, and

VSRYLDWIHGHIRDK, said sequences shown in SEQ ID NO 1 from residue 396 to residue 404, and from residue 396 to residue 410, respectively.

8. A protein C polypeptide comprising no more than 100 amino acid residues and including an amino acid residue sequence represented by the formula: —TRRGDSPWQVVLLDS—, said sequence shown in SEQ ID NO 1 from residue 176 to residue 190, and wherein said polypeptide inhibits activated protein C without inhibiting activated protein C amidolytic activity and without effecting inhibition of activated protein C by $\alpha_1$-antitrypsin.

9. The polypeptide of claim 8 wherein said polypeptide comprises an amino acid residue sequence corresponding to the amino acid residue sequence of protein C shown in SEQ ID NO 1.

10. The polypeptide of claim 8 wherein said polypeptide has an amino acid residue sequence represented by a formula: TRRGDSPWQVVLLDS, said sequence shown in SEQ ID NO 1 from residue 176 to residue 190.

11. A protein C polypeptide comprising no more than 100 amino acid residues and including an amino acid residue sequence represented by the formula: —DIKEVFVHPNYSKST—, said sequence shown in SEQ ID NO 1 from residue 239 to residue 253, and wherein said polypeptide inhibits activated protein C without inhibiting activated protein C amidolytic activity and without effecting inhibition of activated protein C by $\alpha_1$-antitrypsin.

12. The polypeptide of claim 11 wherein said polypeptide comprises an amino acid residue sequence corresponding to the amino acid residue sequence of protein C shown in SEQ ID NO 1.

13. The polypeptide of claim 11 wherein said polypeptide has an amino acid residue sequence represented by a formula: DIKEVFVHPNYSKST, said sequence shown in SEQ ID NO 1 from residue 239 to residue 253.

14. A protein C polypeptide comprising no more than 100 amino acid residues and including an amino acid residue sequence represented by the formula: —VLNFIKIPV—, said sequence shown in SEQ ID NO 1 from residue 317 to residue 325, and wherein said polypeptide inhibits activated protein C without inhibiting activated protein C amidolytic activity and without effecting inhibition of activated protein C by $\alpha_1$-antitrypsin.

15. The polypeptide of claim 14 wherein said polypeptide comprises an amino acid residue sequence corresponding to the amino acid residue sequence of protein C shown in SEQ ID NO 1.

16. The polypeptide of claim 14 wherein said polypeptide has an amino acid residue sequence represented by a formula selected from the group consisting of:

KRNRTFVLNFIKIPV,
VLNFIKIPV,
VLNFIKIPVVPHNEC, and
KRNRTFVLNFIKIPVVPHNEC, said sequences shown in SEQ ID NO 1 from residue 311 to residue 325, from residue 317 to residue 325, from residue 317 to residue 331, and from residue 311 to residue 331, respectively.

17. An antibody comprising antibody molecules that inhibit activated protein C and that immunoreact with:

(a) activated protein C, and (b) a polypeptide having an amino acid residue sequence represented by the formula selected from the group consisting of: YGVYTKVSRYLDWIH, TRRGDSPWQVVLLDS, DIKEVFVHPNYSKST, KRNRTFVLNFIKIPVVPHNEC, said sequences shown in SEQ ID NO 1 from residue 390 to residue 404, from residue 176 to residue 190, from residue 239 to residue 253, and from residue 311 to residue 331, respectively;

but do not immunoreact with the polypeptide having an amino acid residue sequence represented by the formula: PATLSQTIVPICLPDSGLAERE, said sequence shown in SEQ ID NO 1 from residue 266 to residue 287.

18. The antibody of claim 17 wherein said antibody is a monoclonal antibody.

19. A composition comprising an activated protein C-inhibiting amount of a protein C polypeptide according to claims 1, 4, 6, 8, 11 or 14, wherein said polypeptide is dispersed in an acceptable carrier.

20. The composition of claim 19 wherein said activated protein C-inhibiting amount is at least 0.1 weight percent C polypeptide per weight of total composition.

21. A composition comprising an activated protein C-inhibiting amount of an antibody according to claim 17, wherein said antibody is dispersed in an acceptable carrier.

22. The composition of claim 21 wherein said activated protein C-inhibiting amount is at least 0.1 weight percent antibody per weight of total composition.

23. A method for purifying blood coagulation Factor VIII or Factor V protein from plasma comprising the steps of:
  (a) admixing said plasma with an activated protein C-inhibiting amount of a protein C polypeptide according to claims 1, 4, 6, 8, 11 or 14 to form an activated protein C inhibition admixture, and
  (b) recovering said Factor VIII or Factor V protein from said admixture by art-recognized recovery methods.

24. A method for purifying blood coagulation Factor VIII or Factor V protein from plasma comprising the steps of:
  (a) admixing said plasma with an activated protein C-inhibiting amount of an antibody according to claim 17 to form an activated protein C inhibition admixture, and
  (b) recovering said Factor VIII or Factor V protein from said admixture by art-recognized recovery methods.

25. A method for inhibiting activated protein C in an aqueous composition in vitro comprising contacting said aqueous composition with an activated protein C-inhibiting amount of a protein C polypeptide according to claims 1, 4, 6, 8, 11 or 14.

26. A method for inhibiting activated protein C in an aqueous composition in vitro comprising contacting said aqueous composition with an activated protein C-inhibiting amount of an antibody according to claim 17.

27. A method for detecting the presence of a serum protein susceptible to inactivation by activated protein C in an assay reaction admixture comprising (a) admixing an activated protein C-inhibiting amount of a protein C polypeptide according to claims 1, 4, 6, 8, 11 or 14 with an aqueous solution containing the serum protein and an assay buffer compatible with detection of the serum protein to form an in vitro assay reaction admixture and (b) detecting the presence of the serum protein in said admixture.

28. A method for detecting the presence of a serum protein susceptible to inactivation by activated protein C in an assay reaction admixture comprising (a) admixing an activated protein C-inhibiting amount of an antibody according to claim 17 with an aqueous solution containing the serum protein and an assay buffer compatible with detection of the serum protein to form an in vitro assay reaction admixture and (b) detecting the presence of the serum protein in said admixture.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 262 amino acids
        ( B ) TYPE: amino acid
        ( C ) STRANDEDNESS: single
        ( D ) TOPOLOGY: unknown ( i i ) MOLECULE TYPE: protein ( i x ) FEATURE:
        ( A ) NAME/KEY: Region
        ( B ) LOCATION: 1..262
        ( D ) OTHER INFORMATION: /note="In SEQ ID NO 1 is the sequence
        for the PC heavy chain, the amino acid residue positions
        of which begin at position 158 and end at 419."

( x i ) SEQUENCE DESCRIPTION: SEQ ID NO:1:

```
Asp Thr Glu Asp Gln Glu Asp Gln Val Asp Pro Arg Leu Ile Asp Gly
 1               5                  10                  15

Lys Met Thr Arg Arg Gly Asp Ser Pro Trp Gln Val Val Leu Leu Asp
             20                  25                  30

Ser Lys Lys Lys Leu Ala Cys Gly Ala Val Leu Ile His Pro Ser Trp
         35                  40                  45

Val Leu Thr Ala Ala His Cys Met Asp Glu Ser Lys Lys Leu Leu Val
         50                  55                  60
```

```
Arg Leu Gly Glu Tyr Asp Leu Arg Arg Trp Glu Lys Trp Glu Leu Asp
 65              70              75              80

Leu Asp Ile Lys Glu Val Phe Val His Pro Asn Tyr Ser Lys Ser Thr
             85              90              95

Thr Asp Asn Asp Ile Ala Leu Leu His Leu Ala Gln Pro Ala Thr Leu
            100             105             110

Ser Gln Thr Ile Val Pro Ile Cys Leu Pro Asp Ser Gly Leu Ala Glu
        115             120             125

Arg Glu Leu Asn Gln Ala Gly Gln Glu Thr Leu Val Thr Gly Trp Gly
130             135             140

Tyr His Ser Ser Arg Glu Lys Glu Ala Lys Arg Asn Arg Thr Phe Val
145             150             155             160

Leu Asn Phe Ile Lys Ile Pro Val Val Pro His Asn Glu Cys Ser Glu
            165             170             175

Val Met Ser Asn Met Val Ser Glu Asn Met Leu Cys Ala Gly Ile Leu
        180             185             190

Gly Asp Arg Gln Asp Ala Cys Glu Gly Asp Ser Gly Gly Pro Met Val
        195             200             205

Ala Ser Phe His Gly Thr Trp Phe Leu Val Gly Leu Val Ser Trp Gly
210             215             220

Glu Gly Cys Gly Leu Leu His Asn Tyr Gly Val Tyr Thr Lys Val Ser
225             230             235             240

Arg Tyr Leu Asp Trp Ile His Gly His Ile Arg Asp Lys Glu Ala Pro
            245             250             255

Gln Lys Ser Trp Ala Pro
            260
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 6
        ( D ) OTHER INFORMATION: /note="Xaa is either Ala or Lys."

( i x ) FEATURE:
        ( A ) NAME/KEY: Region
        ( B ) LOCATION: 1..15
        ( D ) OTHER INFORMATION: /note="In SEQ ID NO 2 is a PC-derived
            polypeptide that corresponds to amino acid residue
            positions 390 to 404 of PC."

( x i ) SEQUENCE DESCRIPTION: SEQ ID NO:2:

```
Tyr Gly Val Tyr Thr Xaa Val Ser Arg Tyr Leu Asp Trp Ile His
 1               5              10              15
```

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Region
        ( B ) LOCATION: 1..27
        ( D ) OTHER INFORMATION: /note="In SEQ ID NO 3 is a PC-derived polypeptide that corresponds to amino acid residue
positions 384 to 410 of PC."

( x i ) SEQUENCE DESCRIPTION: SEQ ID NO:3:

Ser Gly Leu Leu His Asn Tyr Gly Val Tyr Thr Lys Val Ser Arg Tyr
1               5                   10                  15

Leu Asp Trp Ile His Gly His Ile Arg Asp Lys
            20              25

( 2 ) INFORMATION FOR SEQ ID NO:4:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: unknown ( i i ) MOLECULE TYPE: peptide ( i x ) FEATURE:
         ( A ) NAME/KEY: Region
         ( B ) LOCATION: 1..15
         ( D ) OTHER INFORMATION: /note="In SEQ ID NO 4 is a PC-derived
               polypeptide that corresponds to amino acid residue
               positions 390 to 404 of PC."

( x i ) SEQUENCE DESCRIPTION: SEQ ID NO:4:

Tyr Gly Val Tyr Thr Ala Val Ser Arg Tyr Leu Asp Trp Ile His
1               5                   10                  15

( 2 ) INFORMATION FOR SEQ ID NO:5:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: unknown ( i i ) MOLECULE TYPE: peptide ( i x ) FEATURE:
         ( A ) NAME/KEY: Modified-site
         ( B ) LOCATION: 9
         ( D ) OTHER INFORMATION: /note="Serine has been substituted
               for the originally occurring cysteine in SEQ ID NO
               1."

( i x ) FEATURE:
         ( A ) NAME/KEY: Region
         ( B ) LOCATION: 1..15
         ( D ) OTHER INFORMATION: /note="In SEQ ID NO 5 is a PC-derived
               polypeptide that corresponds to amino acid residue
               positions 188 to 202 of PC."

( x i ) SEQUENCE DESCRIPTION: SEQ ID NO:5:

Leu Asp Ser Lys Lys Lys Leu Ala Ser Gly Ala Val Leu Ile His
1               5                   10                  15

( 2 ) INFORMATION FOR SEQ ID NO:6:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: unknown ( i i ) MOLECULE TYPE: peptide ( i x ) FEATURE:
         ( A ) NAME/KEY: Modified-site
         ( B ) LOCATION: 11
         ( D ) OTHER INFORMATION: /note="Serine has been substituted
               for the originally occurring cysteine in SEQ ID NO
               1."

( i x ) FEATURE:
    ( A ) NAME/KEY: Region
    ( B ) LOCATION: 1..15
    ( D ) OTHER INFORMATION: /note="In SEQ ID NO 6 is a PC-derived
        polypeptide that corresponds to amino acid residue
        positions 202 to 216 of PC."

( x i ) SEQUENCE DESCRIPTION: SEQ ID NO:6:

```
His Pro Ser Trp Val Leu Thr Ala Ala His Ser Met Asp Glu Ser
 1               5                  10                  15
```

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 12
        ( D ) OTHER INFORMATION: /note="Serine has been substituted
            for the originally occurring cysteine in SEQ ID NO
            1."

( i x ) FEATURE:
        ( A ) NAME/KEY: Region
        ( B ) LOCATION: 1..15
        ( D ) OTHER INFORMATION: /note="In SEQ ID NO 7 is a PC-derived
            polypeptide that corresponds to amino acid residue
            positions 266 to 280 of PC."

( x i ) SEQUENCE DESCRIPTION: SEQ ID NO:7:

```
Pro Ala Thr Leu Ser Gln Thr Ile Val Pro Ile Ser Leu Pro Asp
 1               5                  10                  15
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 12
        ( D ) OTHER INFORMATION: /note="Glycine has been
            substituted for the originally occurring cysteine
            in SEQ ID NO 1."

( i x ) FEATURE:
        ( A ) NAME/KEY: Region
        ( B ) LOCATION: 1..15
        ( D ) OTHER INFORMATION: /note="In SEQ ID NO 8 is a PC-derived
            polypeptide that corresponds to amino acid residue
            positions 266 to 280 of PC."

( x i ) SEQUENCE DESCRIPTION: SEQ ID NO:8:

```
Pro Ala Thr Leu Ser Gln Thr Ile Val Pro Ile Gly Leu Pro Asp
 1               5                  10                  15
```

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown ( i i ) MOLECULE TYPE: peptide (ix) FEATURE:
  (A) NAME/KEY: Modified-site
  (B) LOCATION: 13
  (D) OTHER INFORMATION: /note="Serine has been substituted for the originally occurring cysteine in SEQ ID NO 1."

(ix) FEATURE:
  (A) NAME/KEY: Region
  (B) LOCATION: 1..15
  (D) OTHER INFORMATION: /note="In SEQ ID NO 9 is a PC-derived polypeptide that corresponds to amino acid residue positions 333 to 347 of PC."

(xi) SEQUENCE DESCRIPTION: SEQ ID NO:9:

Glu Val Met Ser Asn Met Val Ser Glu Asn Met Leu Ser Ala Gly
1               5                   10                  15

(2) INFORMATION FOR SEQ ID NO:10:

(i) SEQUENCE CHARACTERISTICS:
    (A) LENGTH: 15 amino acids
    (B) TYPE: amino acid
    (C) STRANDEDNESS: single
    (D) TOPOLOGY: unknown (ii) MOLECULE TYPE: peptide (ix) FEATURE:
    (A) NAME/KEY: Modified-site
    (B) LOCATION: 6
    (D) OTHER INFORMATION: /note="Serine has been substituted for the originally occurring cysteine in SEQ ID NO 1."

(ix) FEATURE:
    (A) NAME/KEY: Region
    (B) LOCATION: 1..15
    (D) OTHER INFORMATION: /note="In SEQ ID NO 10 is a PC-derived polypeptide that corresponds to amino acid residue positions 351 to 365 of PC."

(xi) SEQUENCE DESCRIPTION: SEQ ID NO:10:

Asp Arg Gln Asp Ala Ser Glu Gly Asp Ser Gly Gly Pro Met Val
1               5                   10                  15

(2) INFORMATION FOR SEQ ID NO:11:

(i) SEQUENCE CHARACTERISTICS:
    (A) LENGTH: 15 amino acids
    (B) TYPE: amino acid
    (C) STRANDEDNESS: single
    (D) TOPOLOGY: unknown (ii) MOLECULE TYPE: peptide (ix) FEATURE:
    (A) NAME/KEY: Region
    (B) LOCATION: 1..15
    (D) OTHER INFORMATION: /note="In SEQ ID NO 11 is a PC-derived polypeptide that corresponds to amino acid residue positions 404 to 390 of PC, synthesized in reverse orientation."

(xi) SEQUENCE DESCRIPTION: SEQ ID NO:11:

His Ile Trp Asp Leu Tyr Arg Ser Val Lys Thr Tyr Val Gly Tyr
1               5                   10                  15